(12) United States Patent
Suh et al.

(10) Patent No.: US 11,934,039 B2
(45) Date of Patent: Mar. 19, 2024

(54) SURGICAL LOUPES HEAD STRAP

(71) Applicant: The Board of Regents of the University of Nebraska, Lincoln, NE (US)

(72) Inventors: Donny Suh, Omaha, NE (US); James Hermsen, Omaha, NE (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 832 days.

(21) Appl. No.: 16/961,131

(22) PCT Filed: Jan. 16, 2019

(86) PCT No.: PCT/US2019/013777
§ 371 (c)(1),
(2) Date: Jul. 9, 2020

(87) PCT Pub. No.: WO2019/143670
PCT Pub. Date: Jul. 25, 2019

(65) Prior Publication Data
US 2020/0341293 A1    Oct. 29, 2020

Related U.S. Application Data
(60) Provisional application No. 62/618,682, filed on Jan. 18, 2018.

(51) Int. Cl.
  *G02C 3/00*     (2006.01)
  *A61B 90/50*    (2016.01)
(52) U.S. Cl.
  CPC .............. *G02C 3/003* (2013.01); *A61B 90/50* (2016.02); *A61B 2090/502* (2016.02)
(58) Field of Classification Search
  CPC ... G02C 3/003; A61B 90/50; A61B 2090/502; G02B 25/0004
  (Continued)

(56) References Cited

U.S. PATENT DOCUMENTS 3,728,012 A * 4/1973 Downey ................ G02C 3/003
                                                   351/123
3,827,790 A * 8/1974 Wenzel ................. G02C 3/003
                                                   24/3.13
(Continued)

FOREIGN PATENT DOCUMENTS

| DE | 202007009769 U1 * | 1/2008 | ............ G02C 3/003 |
| GB | 919444 | * | 2/1963 | ............ G02C 3/003 |
| GB | 2249191 | * | 4/1992 | ............ G02C 3/003 |

OTHER PUBLICATIONS

Machine translation of DE-202007009769-U1 retrieved electronically from Espacenet May 3, 2023 (Year: 2023).*

(Continued)

*Primary Examiner* — Cara E Rakowski
(74) *Attorney, Agent, or Firm* — Nasr Patent Law LLC; Faisal K. Abou-Nasr

(57) ABSTRACT

A surgical loupes head strap is disclosed. The surgical loupes head strap may include a first monofilament and a second monofilament coupled by at least one sleeve. The surgical loupes head strap may further include a first coupler with a first hole and a second hole, where the first hole is configured to surround and couple to a first end of the first monofilament, and the second hole is configured to surround and couple to at least a portion of a first surgical loupes headgear temple. The surgical loupes head strap may further include a second coupler with a first hole and a second hole, where the first hole is configured to surround and couple to a first end of the second monofilament, and the second hole is configured to surround and couple to at least a portion of a second surgical loupes headgear temple.

9 Claims, 23 Drawing Sheets

(58) Field of Classification Search
USPC .......................................... 351/155; 359/481
See application file for complete search history.

(56) References Cited

U.S. PATENT DOCUMENTS

| | | | |
|---|---|---|---|
| 3,994,990 A | 11/1976 | Foote | |
| 6,736,504 B1 | 5/2004 | Hermsen | |
| 6,764,177 B1* | 7/2004 | Chisolm | G02C 3/006 351/156 |
| 7,467,867 B1 | 12/2008 | Williams | |
| 2002/0133914 A1* | 9/2002 | Scott | G02C 11/00 24/3.3 |
| 2003/0101542 A1 | 6/2003 | Mackay et al. | |
| 2004/0001179 A1* | 1/2004 | Kalbach | G02C 3/003 351/157 |
| 2009/0231699 A1 | 9/2009 | Nakamura | |
| 2010/0177276 A1 | 7/2010 | Spinnato et al. | |
| 2010/0283962 A1 | 11/2010 | Williams | |

OTHER PUBLICATIONS

International Search Report dated Mar. 27, 2019 for PCT/US19/13777.

* cited by examiner

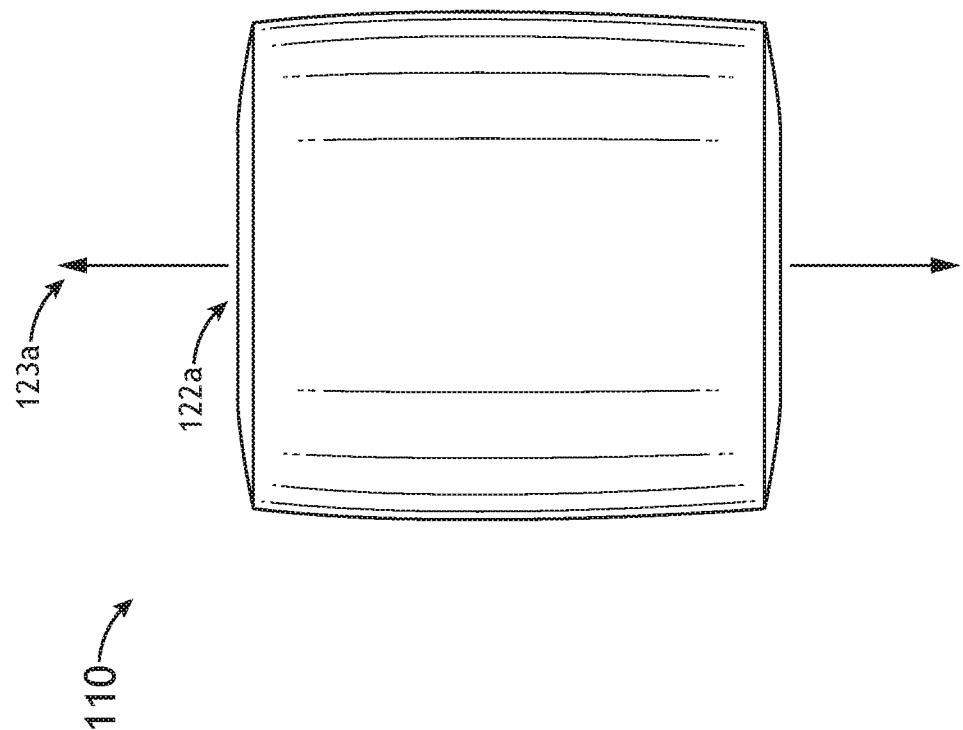

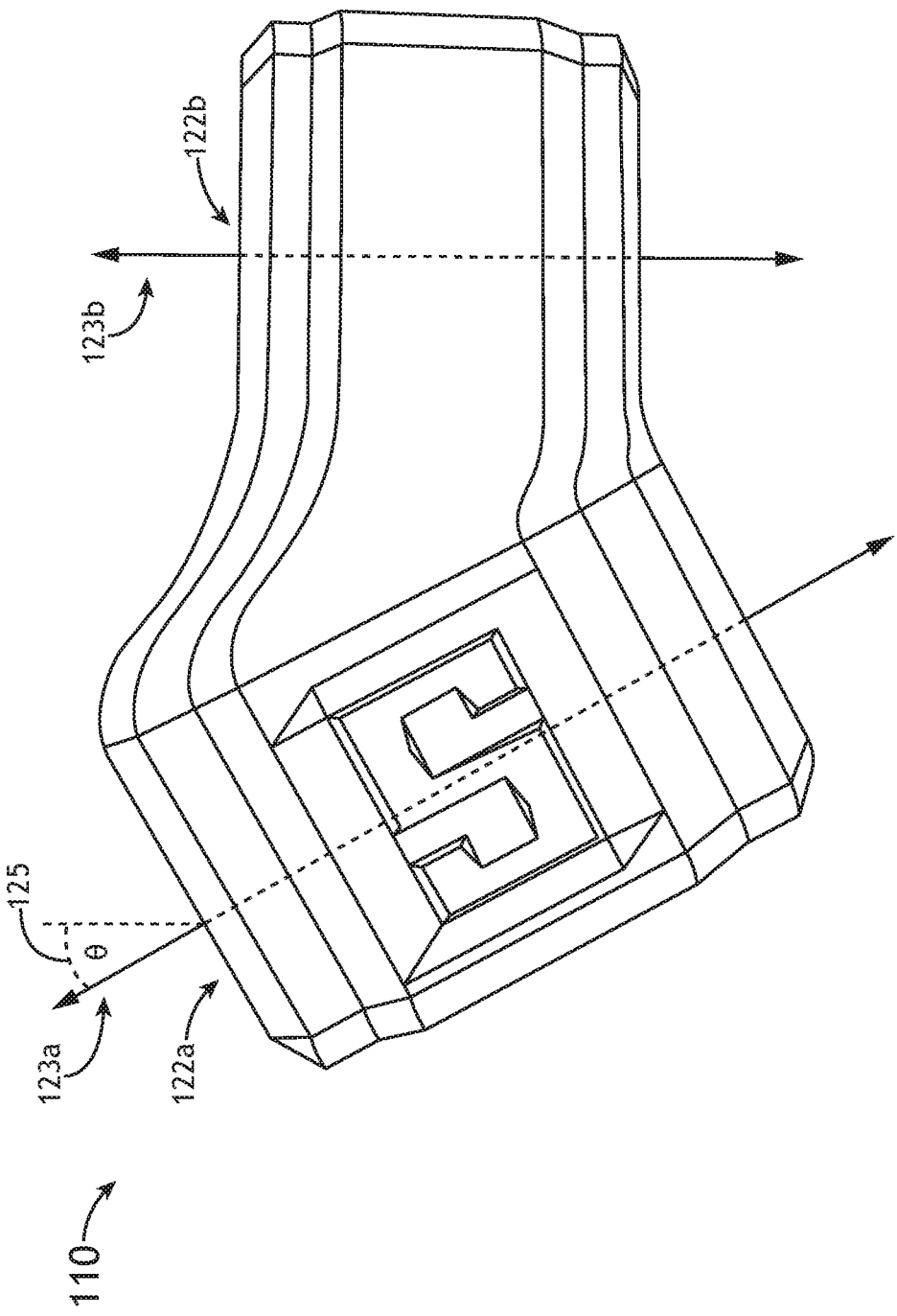

SURGICAL LOUPES HEAD STRAP

CROSS-REFERENCE TO RELATED APPLICATIONS

The present application claims the benefit of U.S. Provisional Application Ser. No. 62/618,682, filed Jan. 18, 2018, and titled "ADJUSTABLE STRAP SYSTEM," which is herein incorporated by reference in its entirety.

BACKGROUND

Many types of specialty eyewear (e.g., surgical loupes) are heavy and often exert non-ergonomic pressure on the wearer, which may result in discomfort or injury. Additionally, many specialty surgical practitioners, including dentists, orthodontists, ophthalmologists, and the like, often have to perform their job functions in poor ergonomic and postural positions. These poor postural and ergonomic positions may be exacerbated by heavy surgical loupes, leading to head, neck, and back discomfort and injuries which may directly impact quality of life, result in lost wages, and even early retirement. Previous approaches which have attempted to make surgical loupes more comfortable exhibit limited utility in that they often result in heavier, bulkier surgical loupes. Accordingly, there is a need for technology that solves one or more of the problems identified above.

SUMMARY

A surgical loupes head strap is disclosed. In embodiments, the surgical loupes head strap includes a first monofilament with a first end and a second end, and a second monofilament with a first end and a second end coupled by at least one sleeve. The surgical loupes head strap may further include a first coupler with a first hole and a second hole, where the first hole is configured to surround and couple to the first end of the first monofilament, and the second hole is configured to surround and couple to at least a portion of a first surgical loupes headgear temple. The surgical loupes head strap may further include a second coupler with a first hole and a second hole, where the first hole is configured to surround and couple to the first end of the second monofilament, and the second hole is configured to surround and couple to at least a portion of a second surgical loupes headgear temple.

A surgical loupes headgear is also disclosed. In embodiments, the surgical loupes headgear includes surgical loupes and a frame configured to support the surgical loupes. The frame may include a first temple and a second temple. The surgical loupes headgear may further include a surgical loupes head strap. The surgical loupes head strap may include a first monofilament with a first end and a second end, and a second monofilament with a first end and a second end coupled by at least one sleeve. The surgical loupes head strap may further include a first coupler with a first hole and a second hole, where the first hole is configured to surround and couple to the first end of the first monofilament, and the second hole is configured to surround and couple to at least a portion of the first temple. The surgical loupes head strap may further include a second coupler with a first hole and a second hole, where the first hole is configured to surround and couple to the first end of the second monofilament, and the second hole is configured to surround and couple to at least a portion of the second temple.

A method for assembling a surgical loupes headgear is also disclosed. In embodiments, the method may include: inserting a first monofilament and a second monofilament into at least one sleeve; coupling a first hole of a first coupler to a first end of the first monofilament; coupling a first hole of a second coupler to a first end of the second monofilament; disposing a first stopper at a second end of the first monofilament; disposing a second stopper at a second end of the second monofilament; coupling at least a portion of a first surgical loupes headgear temple to a second hole of the first coupler; and coupling at least a portion of a second surgical loupes headgear temple to a second hole of the second coupler.

This Summary is provided solely as an introduction to subject matter that is fully described in the Detailed Description and Drawings. The Summary should not be considered to describe essential features nor be used to determine the scope of the Claims. Moreover, it is to be understood that both the foregoing Summary and the following Detailed Description are example and explanatory only and are not necessarily restrictive of the subject matter claimed.

BRIEF DESCRIPTION OF THE DRAWINGS

The detailed description is described with reference to the accompanying figures. The use of the same reference numbers in different instances in the description and the figures may indicate similar or identical items. Various embodiments or examples ("examples") of the present disclosure are disclosed in the following detailed description and the accompanying drawings. The drawings are not necessarily to scale. In general, operations of disclosed processes may be performed in an arbitrary order, unless otherwise provided in the claims.

FIG. 5D is a side elevation view of a coupler in a parallel configuration, in accordance with an example embodiment of the present disclosure.

FIG. 7C is a side elevation view of a coupler in a non-parallel configuration, in accordance with an example embodiment of the present disclosure.

DETAILED DESCRIPTION

Many types of specialty eyewear (e.g., surgical loupes) are heavy and often exert non-ergonomic pressure on the wearer, which may result in discomfort or injury. Specifically, the majority of the weight of surgical loupes rests on the nasal bridge and ears of the wearer. Additionally, many specialty surgical practitioners, including dentists, orthodontists, and ophthalmologists, often have to perform their job functions in poor ergonomic and postural positions. These poor postural and ergonomic positions may be exacerbated by heavy surgical loupes, leading to head, neck, and back discomfort and injuries which may directly impact quality of life, result in lost wages, and even early retirement. Previous approaches have attempted to address posture issues by optimizing the optics and optical angle of surgical loupes. However, these previous approaches have resulted in limited utility in that they often result in heavier, bulkier surgical loupes.

This disclosure is directed to a surgical loupes head strap that solves one or more of the problems identified above. The surgical loupes head strap may be configured to displace the weight of surgical loupes (or other eyewear) from the nasal bridge and ears to the back of the head and neck of the wearer. The surgical loupes head strap may also be adjusted in order to fit a wide variety of head shapes and sizes, as well as to permit a wearer to secure the surgical loupes head strap at an optimal position along the back of the head and/or neck.

Figure 1:
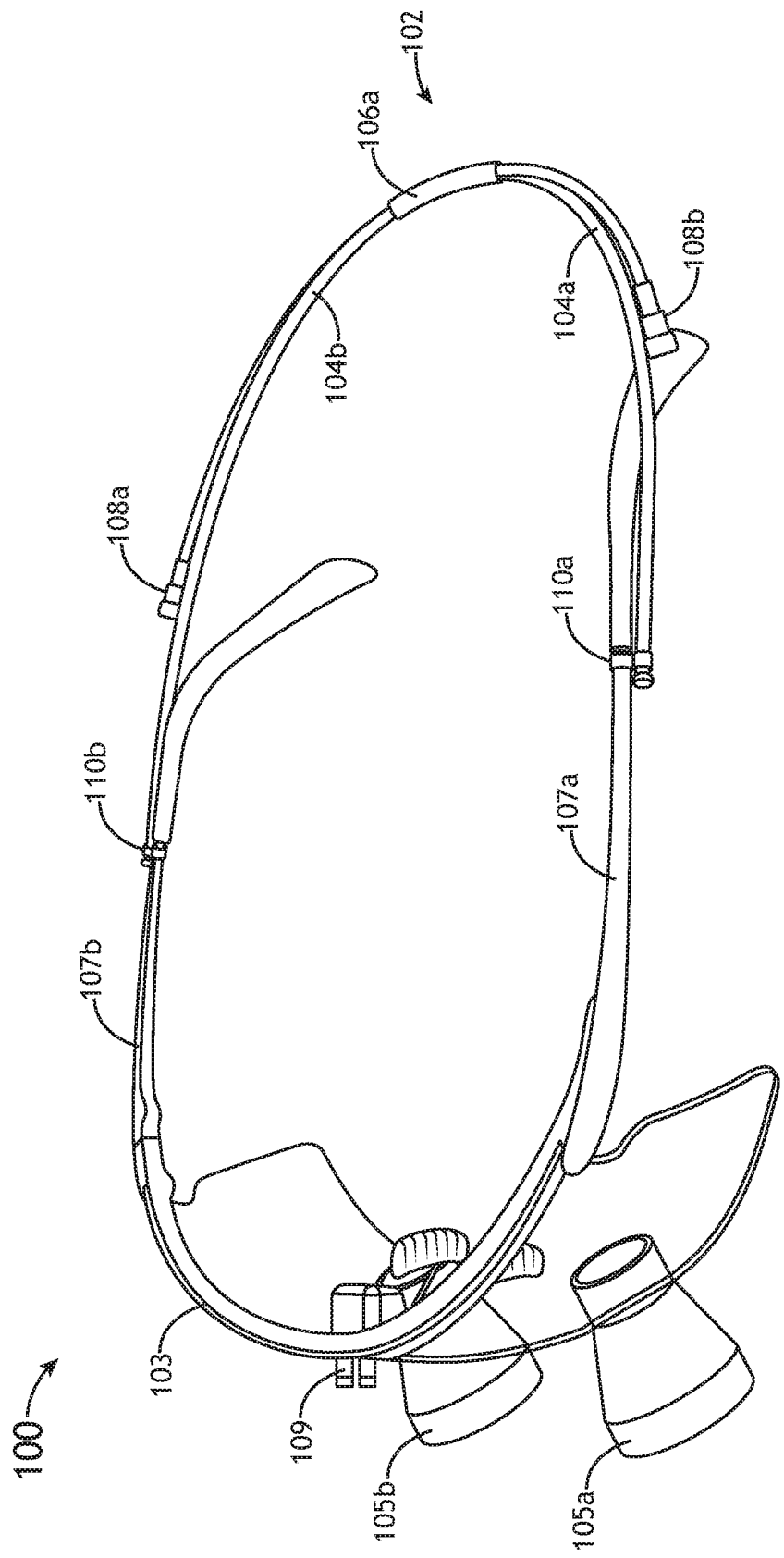
FIG. 1 is a perspective view of surgical loupes headgear, in accordance with an example embodiment of the present disclosure.

FIG. 1 is a perspective view of surgical loupes headgear 100, in accordance with an example embodiment of the present disclosure. In embodiments, the surgical loupes headgear 100 includes a surgical loupes head strap 102, a frame 103, and surgical loupes 105. The frame 103 may be configured to support the surgical loupes 105, as shown in FIG. 1. The surgical loupes 105 may be attached and/or disposed on the frame 103 using any technique known in the art. For example, the surgical loupes 105 may be mechanically or adhesively coupled to the frame 103 and/or to lenses that are supported by the frame 103. The frame 103 may include a bridge 109, a first temple 107a, and a second temple 107b.

As noted previously herein, traditional surgical loupes exert force on a wearer's nasal bridge via nose pads positioned proximate to the bridge 109, and on the wearer's ears via the first temple 107a and the second temple 107b. The surgical loupes headgear 100 further includes a surgical loupes head strap 102 that addresses this problem, among other advantages. The surgical loupes head strap 102 may include, but is not limited to, a first monofilament 104a, a second monofilament 104b, one or more sleeves 106, a first stopper 108a, a second stopper 108b, a first coupler 110a, and a second coupler 110b. In embodiments, the surgical loupes head strap 102 is configured to couple to the first temple 107a and the second temple 107b in order to displace force exerted by the surgical loupes headgear 100 from the nasal bridge and ears of a wearer to the back of the wearer's head and/or neck.

The first monofilament 104a and the second monofilament 104b each may include a first end and a second end. The monofilaments 104 may be formed from any material known in the art. For example, the first monofilament 104a and the second monofilament 104b may be formed from extruded nylon. In embodiments, the monofilaments 104 may be sized such that the surgical loupes head strap 102 may be adjustably sized to fit a wide variety of head shapes and sizes. For example, the first monofilament 104a and the second monofilament 104b may each be eight inches in length. Similarly, the monofilaments 104 may be sized to a particular width/diameter so as to provide sufficient support to support the weight of the surgical loupes headgear 100 on the head of a wearer, without unduly increasing the weight of the surgical loupes headgear 100. For example, the first monofilament 104a and the second monofilament 104b may approximately two millimeters (mm) in diameter.

In embodiments, one or more sleeves 106 are configured to couple the first monofilament 104a and the second monofilament 104b. The one or more sleeves 106 may be formed of any material known in the art. For example, the one or more sleeves 106 may include lengths of polyethylene tubing. In further embodiments, stoppers 108 may be disposed at an end of the first monofilament 104a and the second monofilament 104b. For example, as shown in FIG. 1, a first stopper 108a may be disposed at an end of the first monofilament 104a, and a second stopper 108b may be disposed at an end of the second monofilament 104b. The stoppers 108 may include any stopper known in the art configured to prevent the ends of the monofilaments 104 from sliding through the sleeve 106. In some embodiments, the stoppers 108 may be formed of metal, plastic, rubber, and the like. In other embodiments, the stoppers 108 may be formed by expanding the ends of the monofilaments 104. For instance, the ends of the first monofilament 104a and the second monofilament 104b may be expanded by heating or burning the ends. In other embodiments, the ends of the first monofilament 104a and the second monofilament 104b may be expanded by cutting the ends with a blunt cutter. In this regard, the first stopper 108a and the second stopper 108b may include expanded portions of the monofilaments 104 and/or physical structures disposed at the ends of the monofilaments 104.

The first monofilament 104a may be coupled to the first temple 107a via a first coupler 110a. The first coupler 110a may include a first hole and a second hole, wherein the first hole is configured to surround and couple to an end of the first monofilament 104a, and the second hole is configured to surround and couple to at least a portion of the first temple 107a, as shown in FIG. 1. Similarly, the second monofilament 104b may be coupled to the second temple 107b via a second coupler 110b. The second coupler 110a may also include a first hole and a second hole, wherein the first hole is configured to surround and couple to an end of the second monofilament 104b, and the second hole is configured to surround and couple to at least a portion of the second temple 107b.

The first coupler 110a and the second coupler 110b may be coupled to the first monofilament 104a and the second monofilament 104b using any technique known in the art. In some embodiments, the first coupler 110a and the first monofilament 110b may be welded or soldered together. In other embodiments, the first coupler 110a may be coupled to the first monofilament 104a via an adhesive. In other embodiments, the end of the first monofilament 104a may be expanded to fill a hole of the first coupler 110a, thereby coupling the first monofilament 104a and the first coupler 110a.

Similarly, couplers 110 may be configured to couple to the monofilaments 104 and/or the temples 107 using any technique known in the art. In some embodiments, the couplers 110 may be inelastically deformable and configured to surround and tighten around the monofilaments 104 and/or temples 107. In other embodiments, the couplers 110 may be coupled to the monofilaments 104 and/or temples 107 via one or more heat-shrinking processes. In other embodiments, the couplers 110 may utilize one or more adhesives. The first coupler 110a and the second coupler 110b will be discussed in further detail herein with respect to FIGS. 5A-6D.

As noted previously herein, the surgical loupes head strap 102 may be adjusted in order to fit a wide variety of head shapes and sizes. In this regard, the first monofilament 104a and the second monofilament 104b are configured to be adjustably translated within the one or more sleeves 106 in order to adjust the size of the surgical loupes head strap 102. For example, in order to contract the size of the surgical loupes head strap 102 and optimize a fit for a wearer with a smaller head, the wearer may grasp the first stopper 108a and the second stopper 108b and pull the ends of the first monofilament 104a and the second monofilament 104b "outwards," away from the sleeve 106, thereby translating the first monofilament 104a and the second monofilament 104b within the sleeve 106 and contracting the size of the surgical loupes head strap 102.

Figure 2:
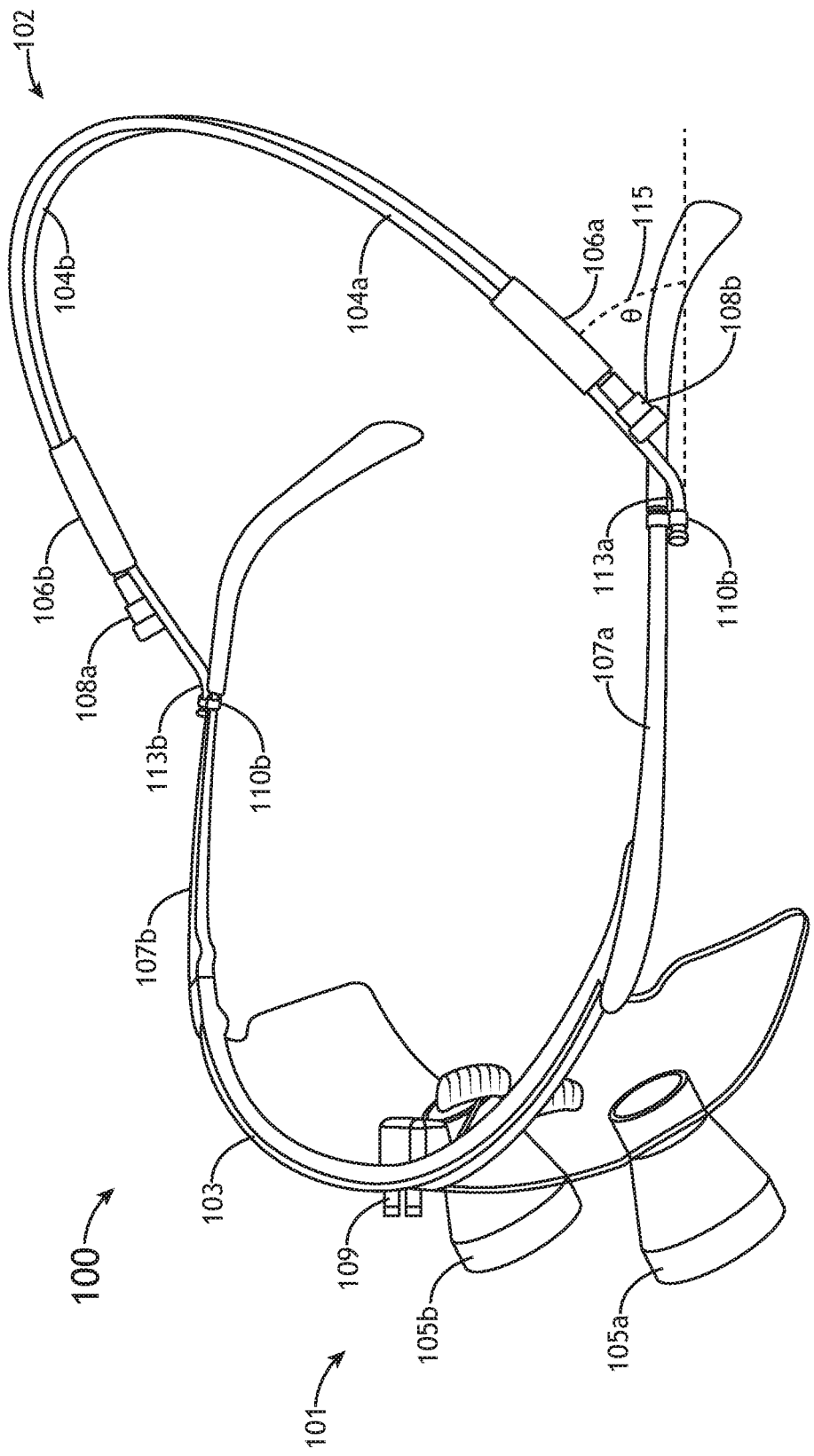
FIG. 2 is a perspective view of surgical loupes headgear, in accordance with an example embodiment of the present disclosure.

FIG. 2 is a perspective view of surgical loupes headgear 100, in accordance with an example embodiment of the present disclosure. It is noted herein that any description associated with the surgical loupes headgear 100 depicted in FIG. 1 may be regarded as applying to the surgical loupes headgear 100 depicted in FIG. 2, unless noted otherwise herein. Similarly, any description associated with the surgical loupes headgear 100 depicted in FIG. 2 may be regarded as applying to the surgical loupes headgear 100 depicted in FIG. 1, unless noted otherwise herein.

As noted previously, surgical loupes headgear 100 may include one or more sleeves 106. For example, as shown in FIG. 2, surgical loupes headgear 100 may include a first sleeve 106a and a second sleeve 106b. In embodiments, including a plurality of sleeves 106 may help retain ends of the monofilaments 104 against the surgical loupes head strap 102. Additionally, including a plurality of sleeves 106 may serve to more firmly couple the first monofilament 104a and the second monofilament 104b in order to prevent inadvertent slipping and/or resizing of the surgical loupes head strap 102.

In embodiments, first monofilament 104a and the second monofilament 104b may include bent portions, as shown in FIG. 2. For example, as shown in FIG. 2, the first monofilament 104a may include a first bent portion 113a defining an offset angle 115, and the second monofilament 104b may include a second bent portion 113b defining the offset angle 115. In embodiments, the first monofilament 104a and the second monofilament 104b may be fabricated to include the bent portions 113 defining a particular offset angle 115. In additional and/or alternative embodiments, the monofilaments 104 may be inelastically deformable, such that the first monofilament 104a and the second monofilament 104b may be bent to a desired angle (e.g., offset angle 115) and hold their shape without becoming brittle or breaking. Fabricating monofilaments 104 with bent portions 113, or providing monofilaments 104 which are inelastically deformable such that a wearer may induce bent portions 113, may allow for the surgical loupes head strap 102 to be customized in order to optimize the fit for various wearers. The offset angle 115 may include any angle between 0 and 90 degrees. For example, the offset angle 115 may be between 10 and 60 degrees, inclusive. While the offset angle 115 defined by the first bent portion 113a and the offset angle 115 defined by the second bent portion 113b are shown to be equal, this is not to be regarded as a limitation of the present disclosure, unless noted otherwise herein. In this regard, the first bent portion 113a may define a first offset angle 115a, and the second bent portion 113b may define a second offset angle 115b, wherein the first offset angle 115a is different from the second offset angle 115b.

Figure 3:
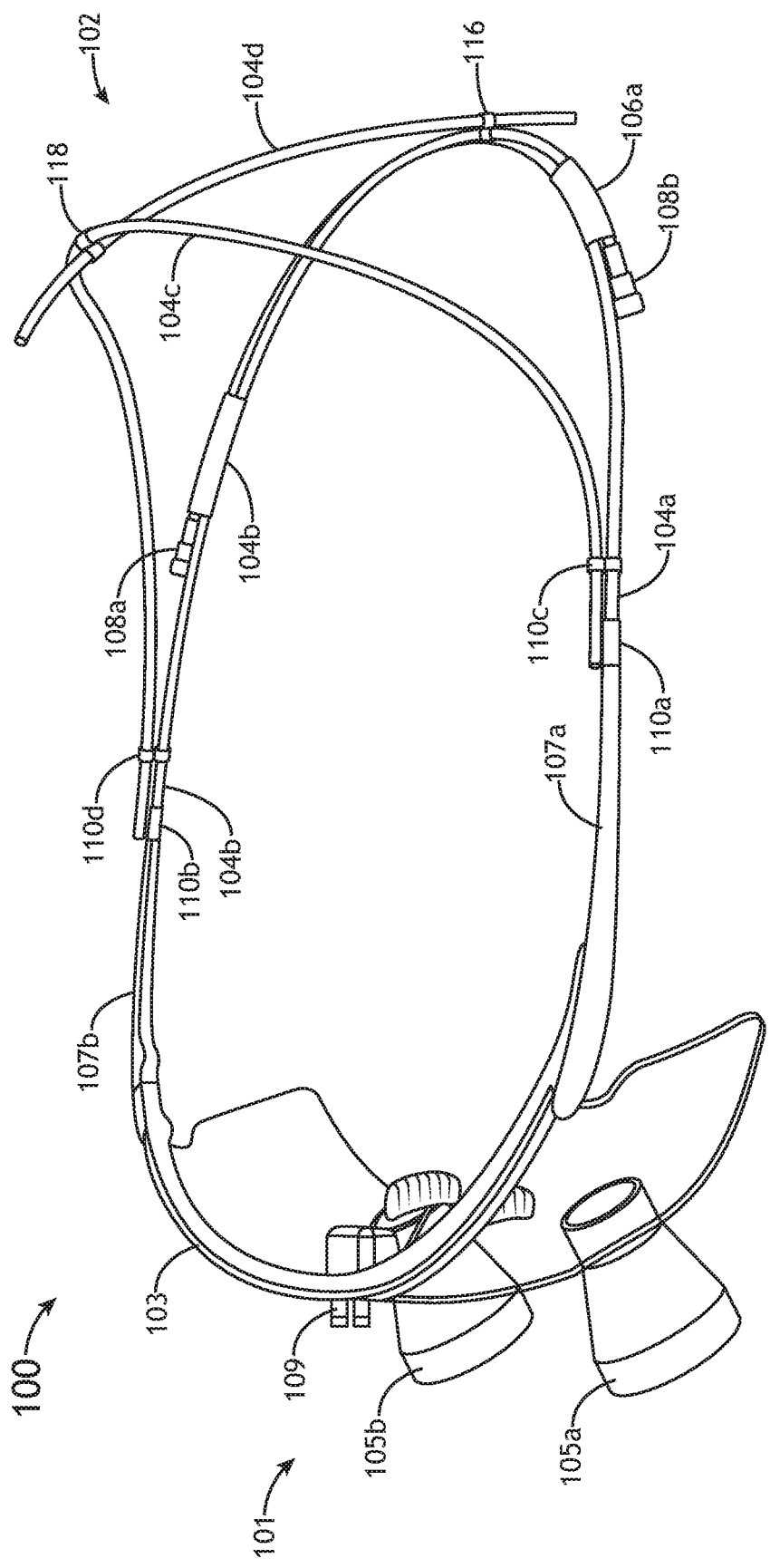
FIG. 3 is a perspective view of surgical loupes headgear, in accordance with an example embodiment of the present disclosure.

FIG. 3 is a perspective view of surgical loupes headgear 100, in accordance with an example embodiment of the present disclosure. It is noted herein that any description associated with the surgical loupes headgear 100 depicted in FIGS. 1-2 may be regarded as applying to the surgical loupes headgear 100 depicted in FIG. 3, unless noted otherwise herein. Similarly, any description associated with the surgical loupes headgear 100 depicted in FIG. 3 may be regarded as applying to the surgical loupes headgear 100 depicted in FIGS. 1-2, unless noted otherwise herein.

Surgical loupes head strap 102 may include additional monofilaments 104 configured to support the surgical loupes headgear 100 on the head of a wearer. For example, as shown in FIG. 3, surgical loupes head strap 102 may include a third monofilament 104c configured to support the surgical loupes headgear 100 by contacting an upper portion a wearer's head. The third monofilament 104c may be coupled to the first monofilament 104a via a coupler 110c, and may be coupled to the second monofilament 104b via a coupler 110d. In some embodiments, surgical loupes head strap 102 may further include a fourth monofilament 104d configured to support the surgical loupes headgear 110 by contacting the back of a wearer's head in a vertical orientation. The fourth monofilament 104d may be coupled to the first monofilament 104a and/or the second monofilament 104b via a coupler 116, and may be coupled to the third monofilament 104c via a coupler 118. In embodiments, the various monofilaments 104 (e.g., third monofilament 104c, fourth monofilament 104d) may be adjustably translated within the couplers (e.g., coupler 110c, 110d, 116, 118) so as to adjust the relative size of the surgical loupes head strap 102 and optimize the fit of the surgical loupes headgear 100 on a wearer.

Figure 4:
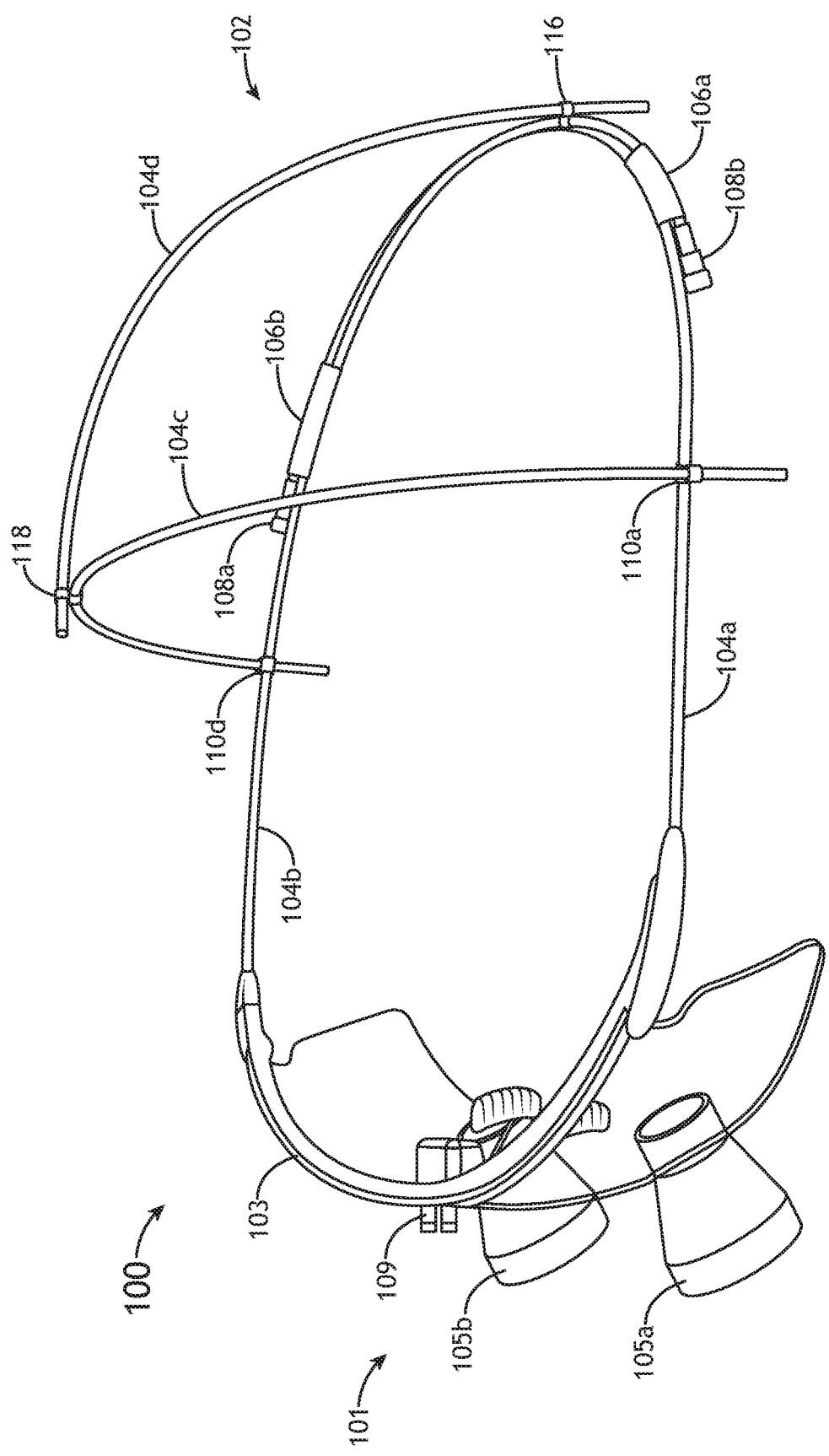
FIG. 4 is a perspective view of surgical loupes headgear, in accordance with an example embodiment of the present disclosure.

FIG. 4 is a perspective view of surgical loupes headgear 100, in accordance with an example embodiment of the present disclosure. It is noted herein that any description associated with the surgical loupes headgear 100 depicted in FIGS. 1-3 may be regarded as applying to the surgical loupes headgear 100 depicted in FIG. 4, unless noted otherwise herein. Similarly, any description associated with the surgical loupes headgear 100 depicted in FIG. 4 may be regarded as applying to the surgical loupes headgear 100 depicted in FIGS. 1-3, unless noted otherwise herein.

In embodiments, the surgical loupes head strap 102 may be directly coupled to the frame 103. For example, as shown in FIG. 3, the first monofilament 104a and the second monofilament 104b may be directly coupled to the frame 103 of the surgical loupes headgear 100. This may be compared to the surgical loupes headgear 100 depicted in FIGS. 1-3, in which the first monofilament 104a and the second monofilament 104b are coupled to a first temple 107a and a second temple 107b of the frame 103, respectively. Coupling the first monofilament 104a and the second monofilament 104b directly to the frame 103 may reduce the overall weight of the surgical loupes headgear 100, and may further optimize the fit for a wearer.

Figure 5A:
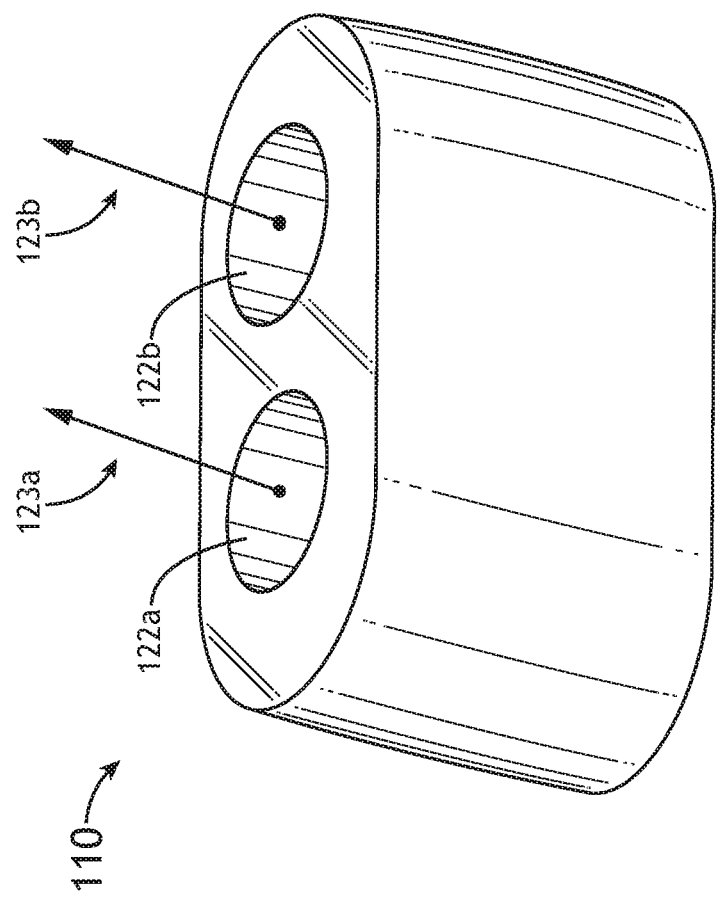
FIG. 5A is a perspective view of a coupler in a parallel configuration, in accordance with an example embodiment of the present disclosure.

FIG. 5A is a perspective view of a coupler 110 in a parallel configuration, in accordance with an example embodiment of the present disclosure. The coupler 110 may include a first hole 122a and a second hole 122b. As shown in FIG. 5A, a first central axis 123a of the first hole 122a and a second central axis 123b of the second hole 122b may be parallel. As it is used throughout the present disclosure, a coupler 110 in which the first central axis 123a and the second central axis 123b are parallel may be referred to as a coupler 110 with a "parallel configuration." As noted previously herein, the coupler 110 may be configured to couple a monofilament 104 and a temple 107 of the surgical loupes headgear 100. For example, the first hole 122a may be configured to surround and couple to a first monofilament 104a, and the second hole 122b may be configured to surround and couple to at least a portion of a first temple 107a, thereby coupling the first monofilament 104a to the first temple 107a.

Figure 5B:
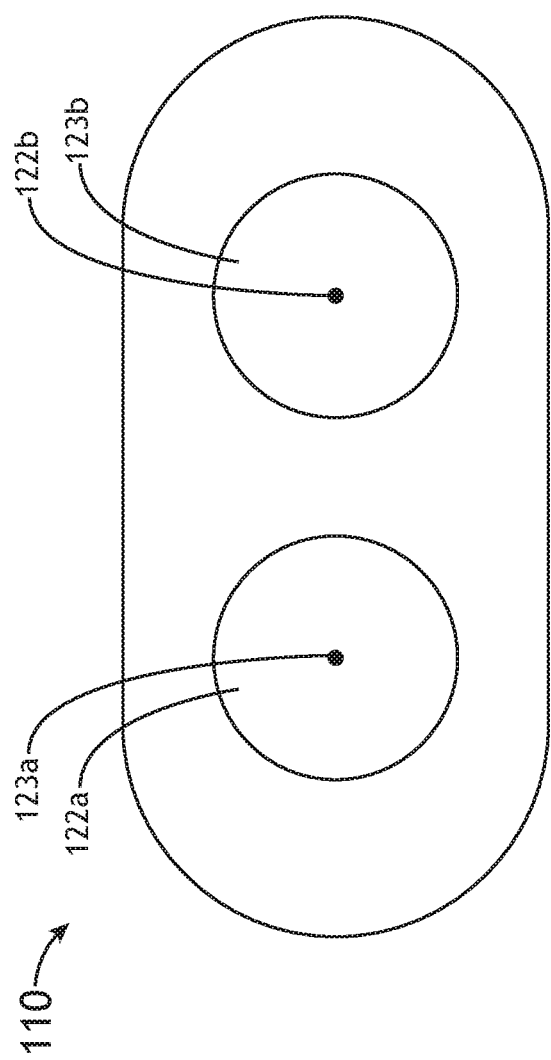
FIG. 5B is a top view of a coupler in a parallel configuration, in accordance with an example embodiment of the present disclosure.

FIG. 5B is a top view of a coupler 110 in a parallel configuration, in accordance with an example embodiment of the present disclosure. While holes 122a, 122b are shown and described throughout as completely enclosed channels/holes through couplers 110, this is not a limitation of the present disclosure, unless noted otherwise herein. In additional and/or alternative embodiments, holes 122a, 122b may include "grooves" which include at least one opening. For example, in embodiments where hole 122a includes a groove, a portion of the body of coupler 110 defining the outer left wall of hole 122a may be missing, thereby causing hole 122a not to be completely enclosed. Using holes 122 that include "grooves" (e.g., one or more openings) may allow the coupler 110 to be "clicked" or "snapped" onto various components of the present disclosure (e.g., monofilaments 104, temples 107, and the like). Furthermore, embodiments where holes 122 include grooves may allow for couplers to be easily and efficiently attached, detached, and adjusted.

Figure 5C:
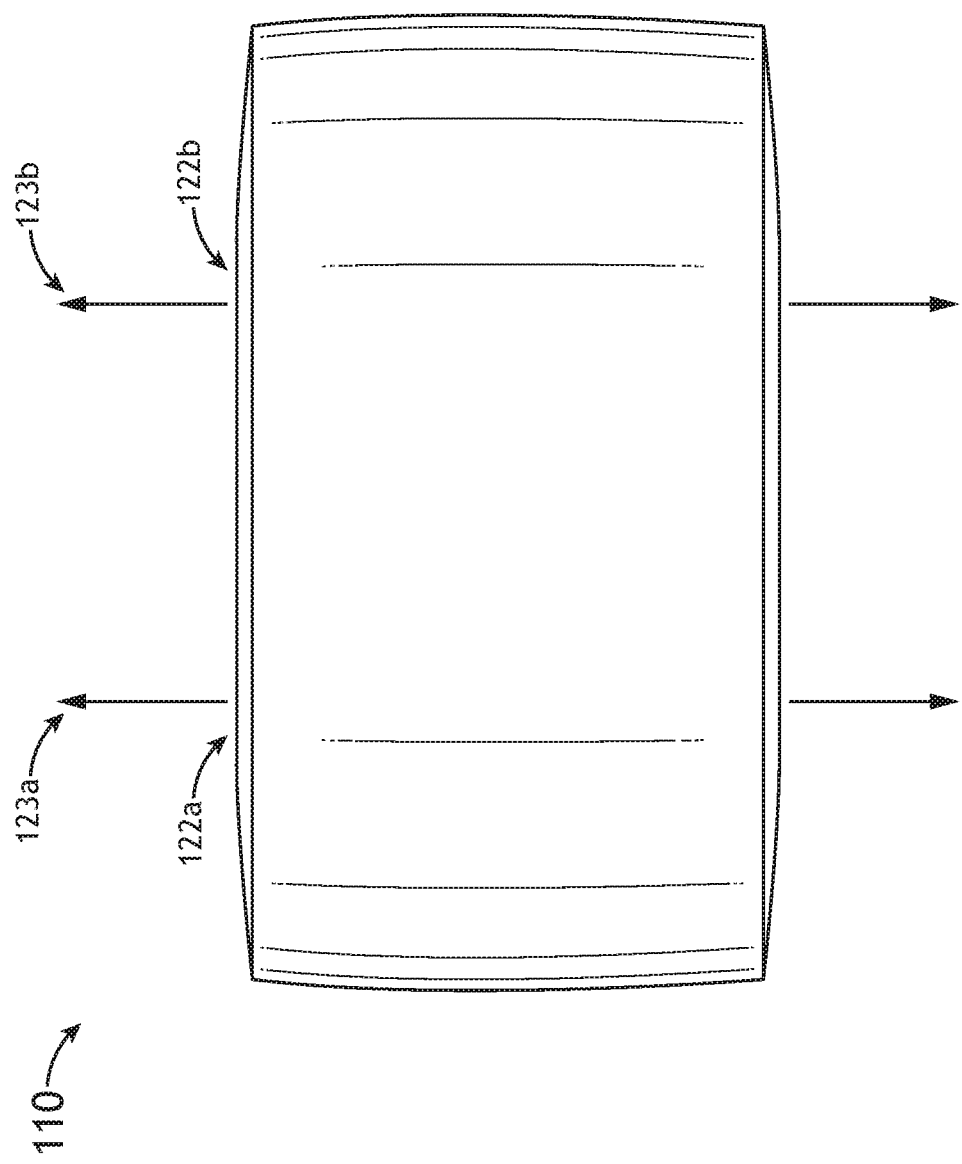
FIG. 5C is a side elevation view of a coupler in a parallel configuration, in accordance with an example embodiment of the present disclosure.

FIG. 5C is a side elevation view of a coupler 110 in a parallel configuration, in accordance with an example embodiment of the present disclosure. FIG. 5D is a side elevation view of a coupler 110 in a parallel configuration, in accordance with an example embodiment of the present disclosure. As may be seen in FIGS. 5B-5D, in a parallel configuration, a first central axis 123a of a first hole 122a and a second central axis 123b of a second hole 122b are parallel.

Figure 6A:
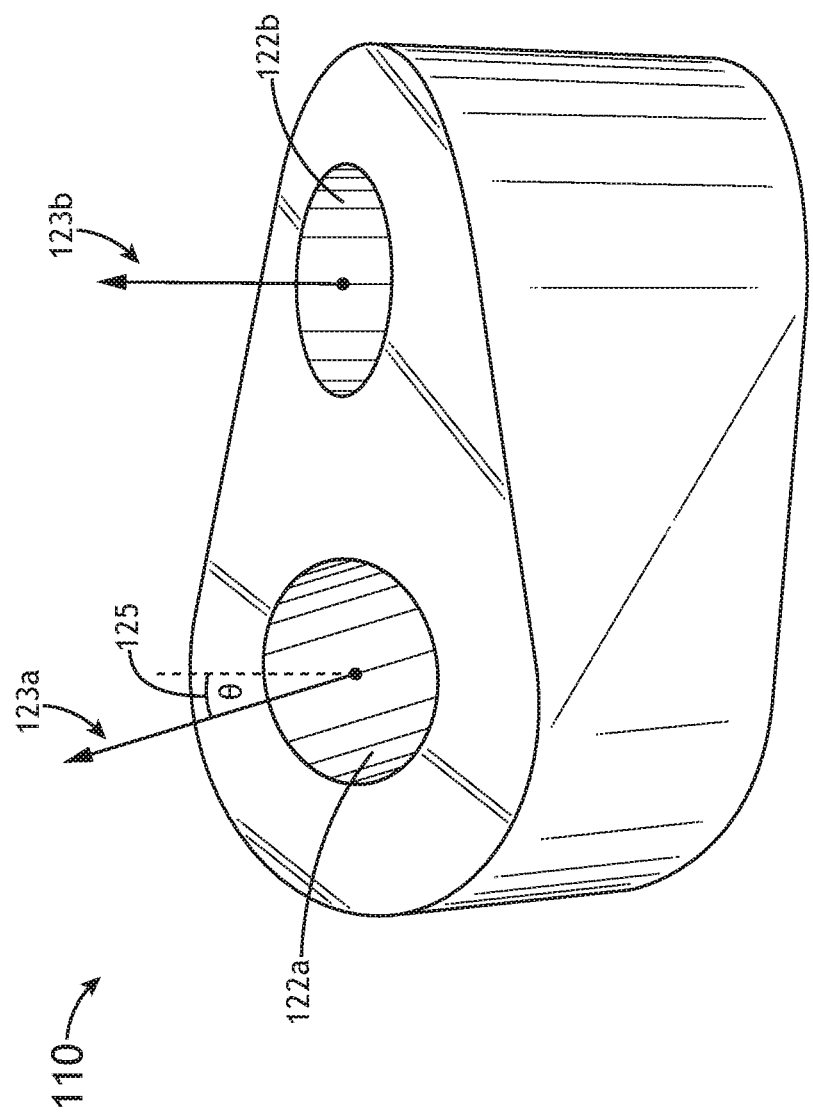
FIG. 6A is a perspective view of a coupler in a non-parallel configuration, in accordance with an example embodiment of the present disclosure.

FIG. 6A is a perspective view of a coupler 110 in a non-parallel configuration, in accordance with an example embodiment of the present disclosure. It is noted herein that any description associated with coupler 110 depicted in FIGS. 5A-5D may be regarded as applying to the coupler 110 depicted in FIGS. 6A-6D to the extent applicable, unless noted otherwise herein. Similarly, any description associated with the coupler 110 depicted in FIGS. 6A-6D may be regarded as applying to the coupler 110 depicted in FIGS. 5A-5D to the extent applicable, unless noted otherwise herein.

The coupler 110 may include a first hole 122a and a second hole 122b. As shown in FIG. 6A, a central axis 123a of the first hole 122a and a central axis 123b of the second hole 122b may be non-parallel (e.g., oblique or perpendicular). As it is used throughout the present disclosure, a coupler 110 in which the central axis 123a and the central axis 123b are non-parallel may be referred to as a coupler 110 with a "non-parallel configuration." In embodiments, a central axis 123a and a central axis 123b are offset by an offset angle 125. The offset angle 125 may include any offset angle between 0 and 90 degrees. For example, the offset angle 125 may be between 10 and 60 degrees, inclusive.

As noted previously herein, the coupler 110 may be configured to couple a monofilament 104 and a temple 107 of the surgical loupes headgear 100. For example, the first hole 122a may be configured to surround and couple to a first monofilament 104a, and the second hole 122b may be configured to surround and couple to at least a portion of a first temple 107a, thereby coupling the first monofilament 104a to the first temple 107a. It is further noted herein that a coupler 110 in a non-parallel configuration may be configured to induce an offset angle 125 between the components coupled by the coupler 110. For instance, referring again to the example above, a coupler 110 in a non-parallel configuration may induce an offset angle 125 between the first monofilament 104a and the first temple 107a. Using a coupler 110 in a non-parallel configuration may be an additional or alternative method of inducing an offset angle between a monofilament 104 and a temple 107 to the bent portions 113 depicted in FIG. 2.

Figure 6B:
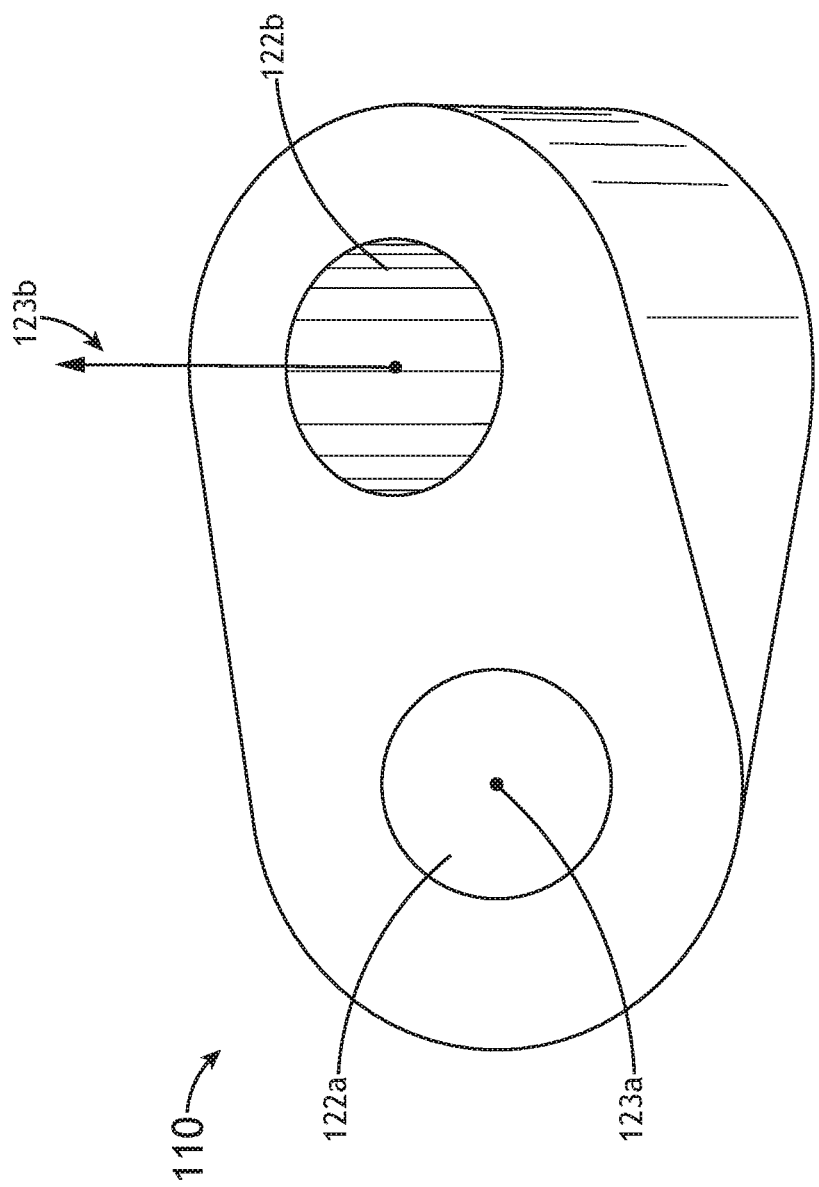
FIG. 6B is a top view of a coupler in a non-parallel configuration, in accordance with an example embodiment of the present disclosure.
Figure 6C:
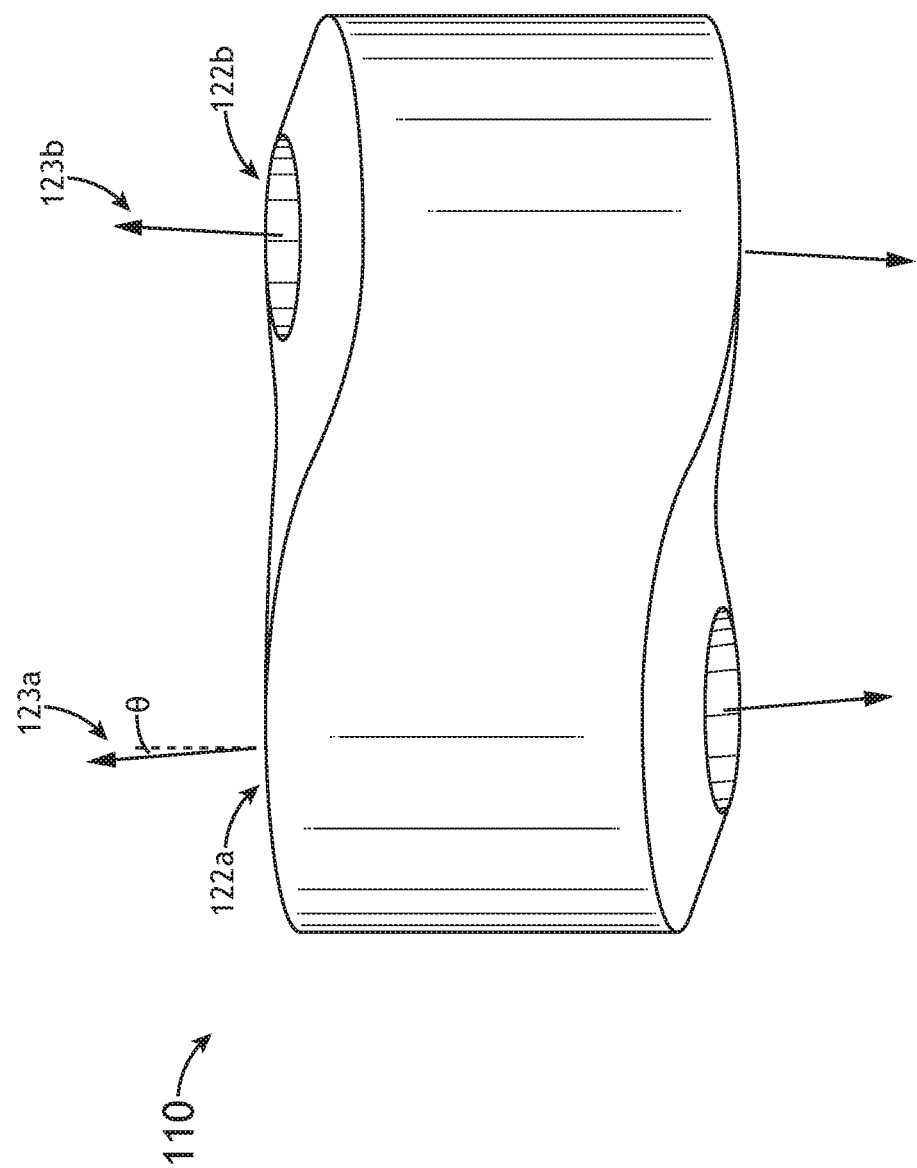
FIG. 6C is a side elevation view of a coupler in a non-parallel configuration, in accordance with an example embodiment of the present disclosure.
Figure 6D:
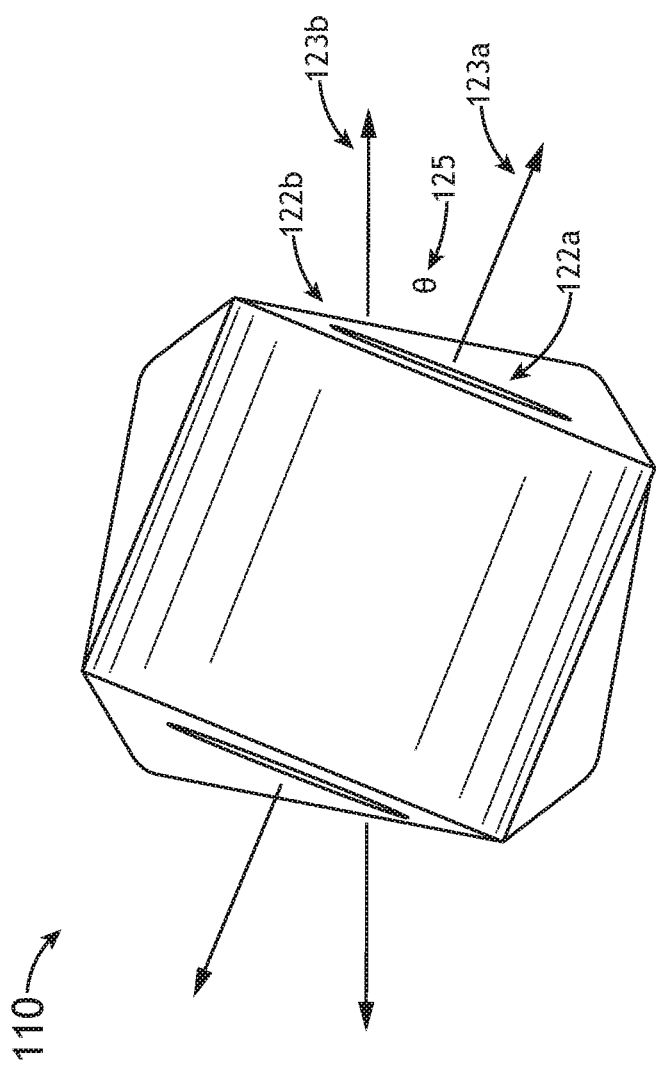
FIG. 6D is a side elevation view of a coupler in a non-parallel configuration, in accordance with an example embodiment of the present disclosure.

FIG. 6B is a top view of a coupler 110 in a non-parallel configuration, in accordance with an example embodiment of the present disclosure. FIG. 6C is a side elevation view of a coupler 110 with a non-parallel configuration, in accordance with an example embodiment of the present disclosure. FIG. 6D is a side elevation view of a coupler 110 with a non-parallel configuration, in accordance with an example embodiment of the present disclosure. In embodiments, the offset angle 125 between the central axis 123a of the first hole 122a and the central axis 123b of the second hole 122b may be in the range of 10 to 60 degrees (e.g., approximately 30 degrees).

Figure 7A:
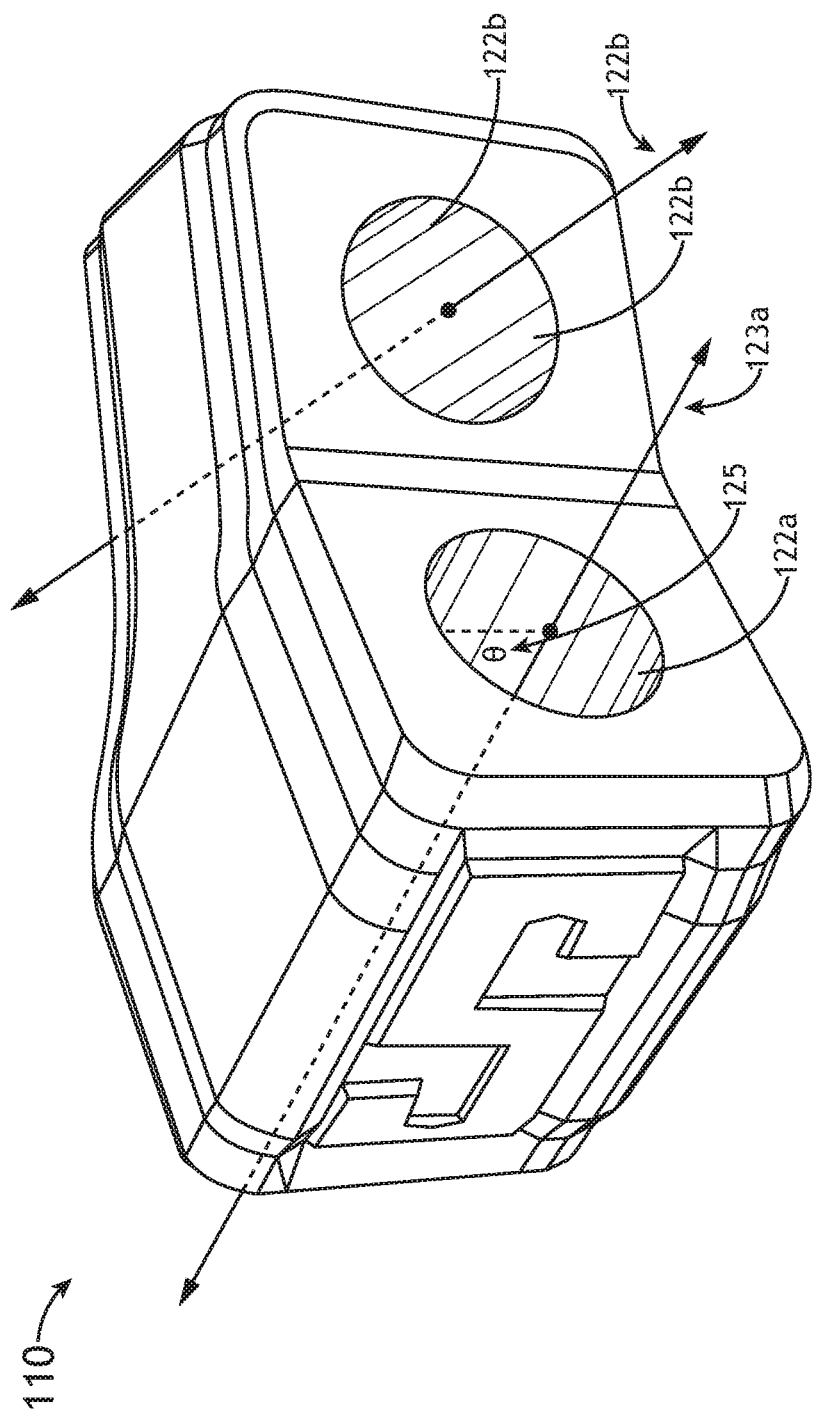
FIG. 7A is a perspective view of a coupler in a non-parallel configuration, in accordance with an example embodiment of the present disclosure.

FIG. 7A is a perspective view of a coupler 110 in a non-parallel configuration, in accordance with an example embodiment of the present disclosure. Coupler 110 depicted in FIGS. 7A-7C may illustrate an additional and/or alternative embodiment of the couplers 110 illustrated in FIGS.

5A-6D. In this regard, any description associated with the couplers 110 illustrated in FIGS. 5A-6D may be regarded as applying to the couplers 110 illustrated in FIGS. 7A-7C to the extent applicable, unless noted otherwise herein.

The coupler 110 may include a first hole 122a and a second hole 122b. A central axis 123a of the first hole 122a and a central axis 123b of the second hole 122b may be non-parallel (e.g., oblique or perpendicular). For instance, as shown in FIG. 7A, central axis 123a and central axis 123b are non-parallel. In embodiments, a central axis 123a and a central axis 123b are offset by an offset angle 125. The offset angle 125 may include any offset angle between 0 and 90 degrees. For example, the offset angle 125 may be between 10 and 60 degrees, inclusive.

Figure 7B:
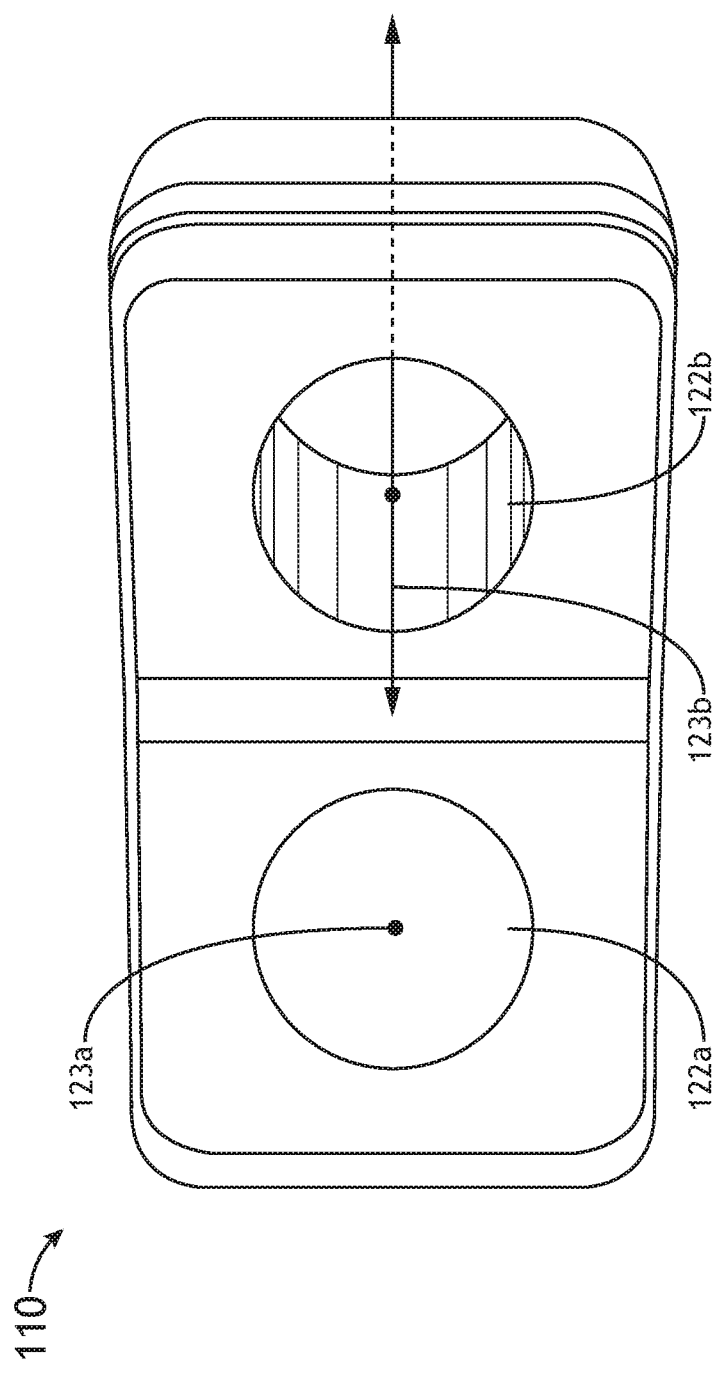
FIG. 7B is a top view of a coupler in a non-parallel configuration, in accordance with an example embodiment of the present disclosure.

FIG. 7B is a top view of a coupler 110 in a non-parallel configuration, in accordance with an example embodiment of the present disclosure. FIG. 7C is a side elevation view of a coupler 110 in a non-parallel configuration, in accordance with an example embodiment of the present disclosure. In embodiments, the length of the first hole 122a may be the same or different as the length of the second hole 122b. For example, in some embodiments, the length of the second hole 122b may be shorter than the length of the first hole 122a, as shown in FIG. 7C.

Figure 8A:
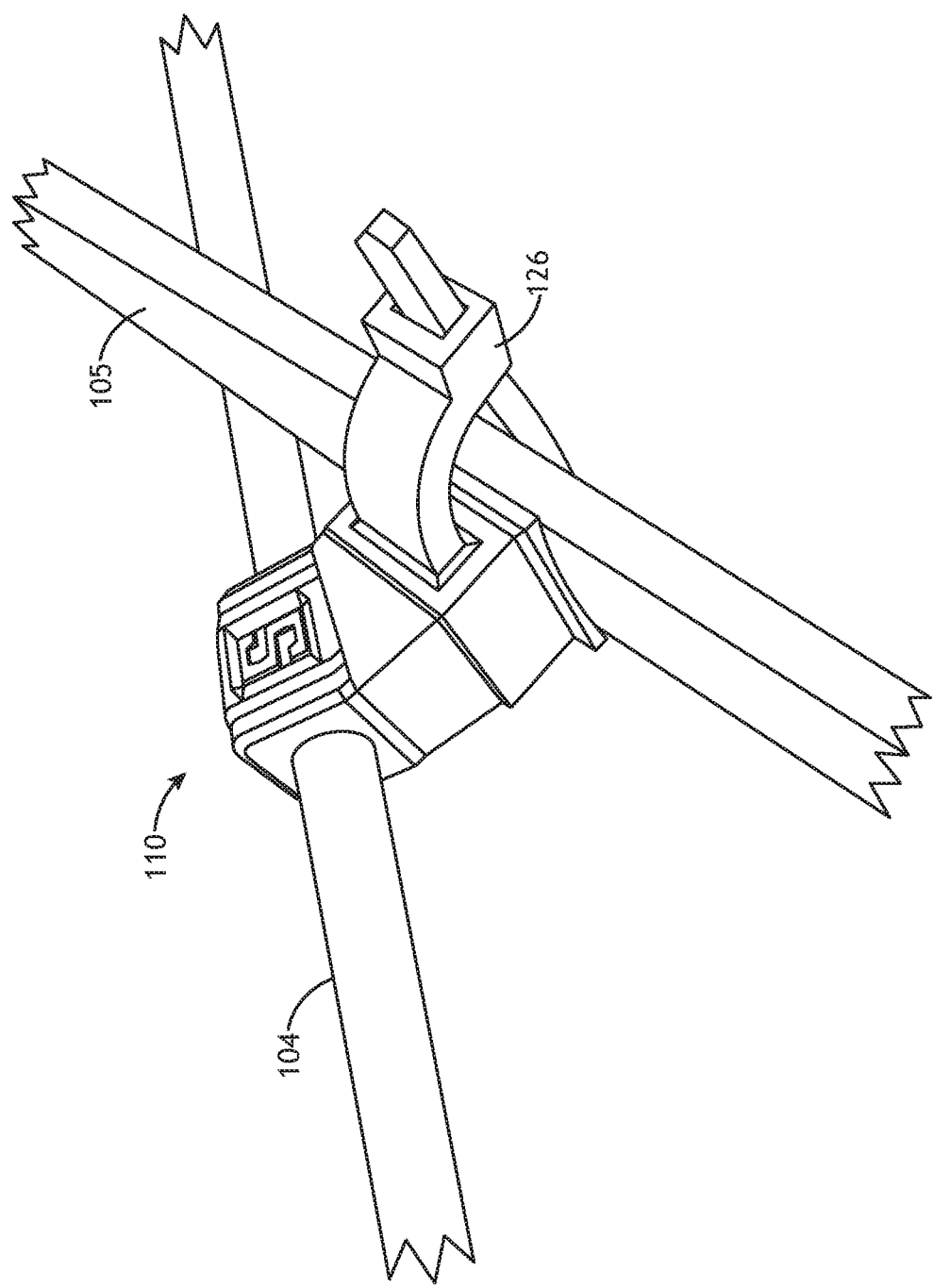
FIG. 8A illustrates an adjustable coupler, in accordance with an example embodiment of the present disclosure.

FIG. 8A illustrates an adjustable coupler 110, in accordance with an example embodiment of the present disclosure. In embodiments, coupler 110 may be a "universal coupler." In some embodiments, at least one hole 122 of a coupler 110 may include an adjustable coupler 126. The adjustable coupler 126 may include any adjustable coupler known in the art. For example, as shown in FIG. 8A, an adjustable coupler 126 may include a zip tie. In other embodiments, the adjustable coupler 126 may include a Velcro-based adjustable coupler 126, an adhesive-based adjustable coupler 126, a strap, and the like. Using an adjustable coupler 126 may allow the coupler 110 to fit temples 107 of varying shapes and sizes. Furthermore, an adjustable coupler 126 may allow a wearer to quickly and efficiently attach/detach a surgical loupes head strap 102 from a surgical loupes headgear 100, adjust how a monofilament 104 is coupled to a temple 107, and may allow a surgical loupes head strap 102 to be transitioned between various surgical loupes headgear 100.

Figure 8B:
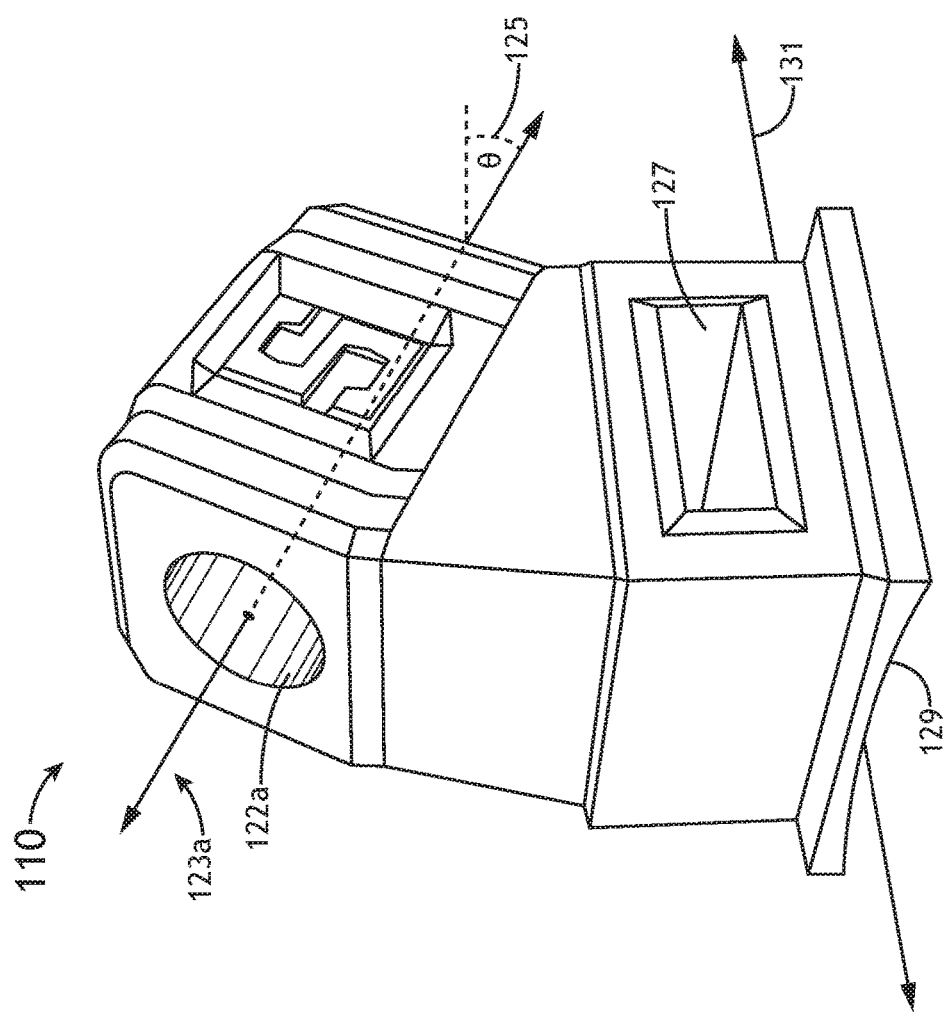
FIG. 8B is a perspective view of a portion of a coupler, in accordance with an example embodiment of the present disclosure.

FIG. 8B is a perspective view of a portion of an adjustable coupler 110, in accordance with an example embodiment of the present disclosure. In embodiments, coupler 110 includes a first hole 122a and a slot 127. The slot 127 may be configured to receive an adjustable coupler 126. For example, in some embodiments, the adjustable coupler 126 may include a zip tie, as shown in FIG. 8A. In other embodiments, the adjustable coupler 126 may include a Velcro-based adjustable coupler 126, an adhesive-based adjustable coupler, a strap, a string, and the like. In this regard, the adjustable coupler 126 disposed within the slot 127 may make up a second hole of the coupler 110. In operation, an adjustable coupler 126 may be inserted within the slot 127 and wrapped around at least a portion of a temple 107 in order to couple the coupler 110 to the temple 107, as shown in FIG. 8A.

Figure 8C:
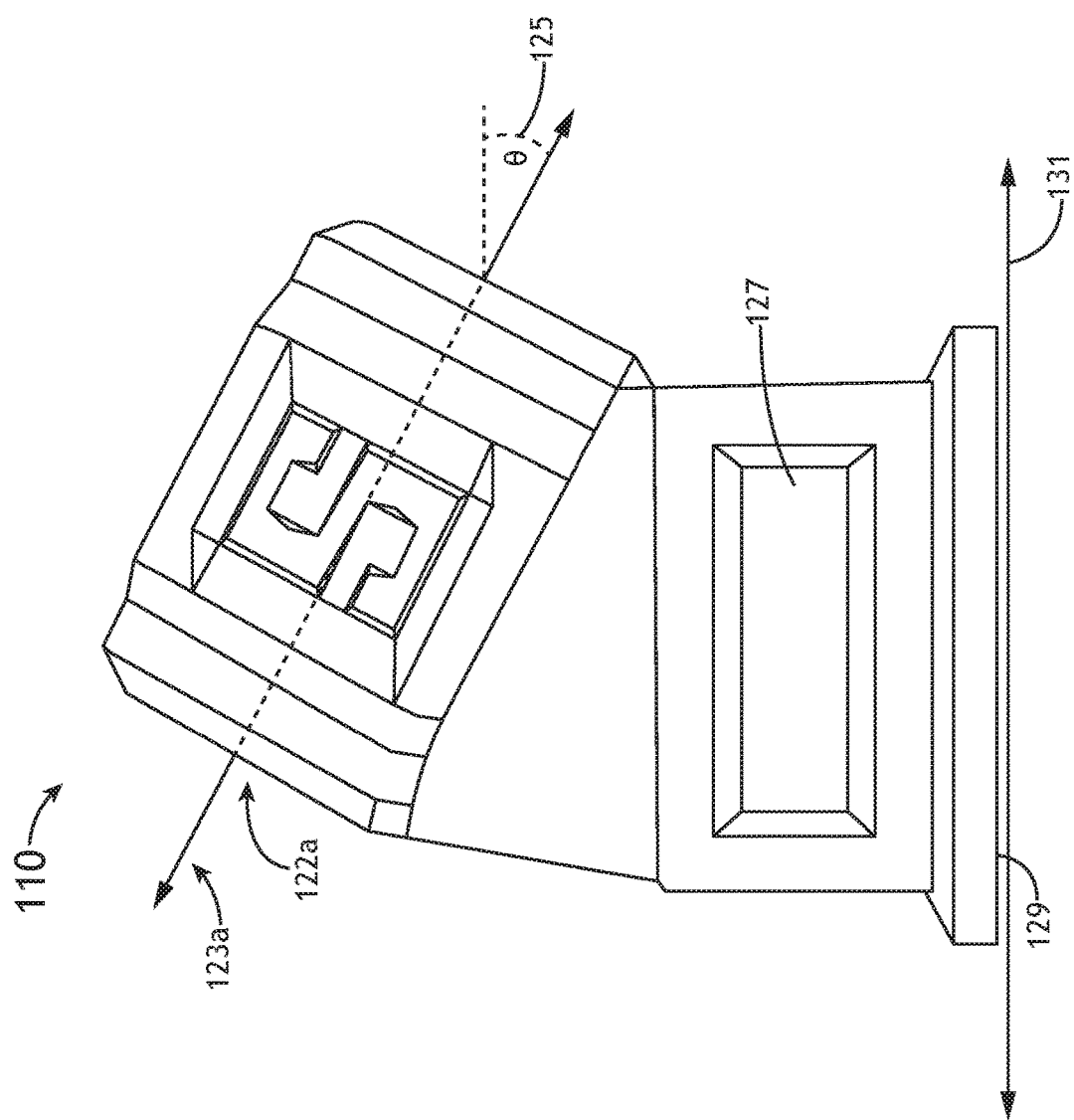
FIG. 8C is a side view of a portion of a coupler, in accordance with an example embodiment of the present disclosure.

FIG. 8C is a side view of a portion of a coupler 110, in accordance with an example embodiment of the present disclosure. In embodiments, coupler 110 may include a surface 129 which is configured to be disposed against and/or positioned adjacent to a temple 107. In this regard, surface 129 may positioned adjacent to a temple 107 along a temple axis 131. In some embodiments, the central axis 123a of the first hole 122a and the temple axis 131 may be non-parallel (e.g., oblique or perpendicular), as shown in FIG. 8C. In this regard, the central axis 123a and the temple axis 131 may be offset by an offset angle 125. In additional and/or alternative embodiments, the central axis 123a and the temple axis 131 may be parallel.

Figure 9A:
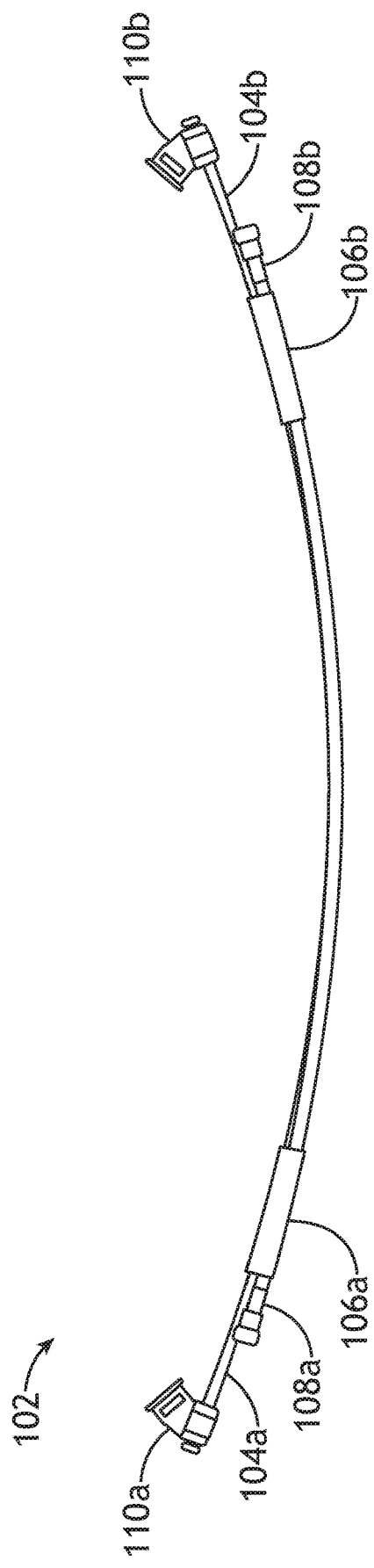
FIG. 9A illustrates a surgical loupes head strap including sleeves configured to couple a first monofilament and a second monofilament, in accordance with an example embodiment of the present disclosure.

FIG. 9A illustrates a surgical loupes head strap 102 including sleeves 106 configured to couple a first monofilament 104a and a second monofilament 104b, in accordance with an example embodiment of the present disclosure. In embodiments, the surgical loupes head strap 102 may include, but is not limited to, a first monofilament 104a, a second monofilament 104b, a first sleeve 106a, a second sleeve 106b, a first stopper 108a, a second stopper 108b, a first coupler 110a, and a second coupler 110b.

Figure 9B:
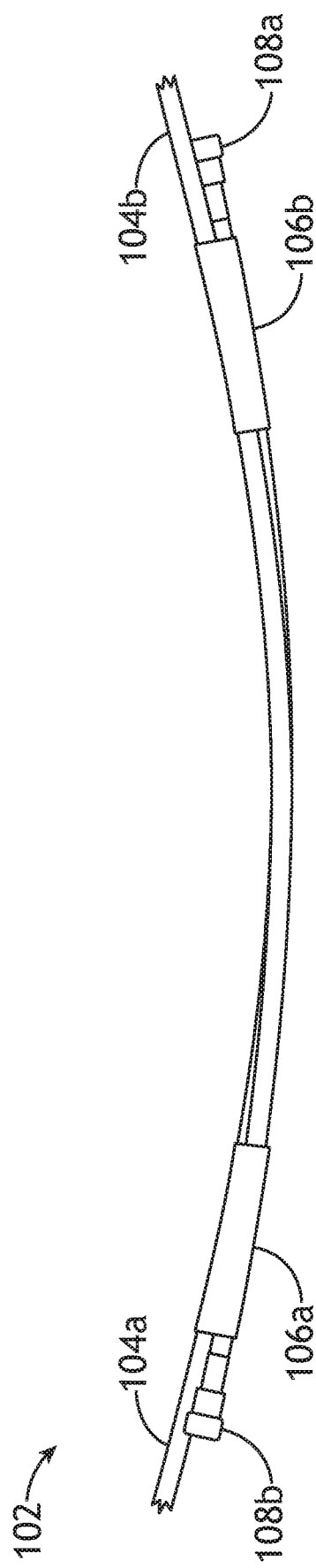
FIG. 9B illustrates a surgical loupes head strap including sleeves configured to couple a first monofilament and a second monofilament, in accordance with an example embodiment of the present disclosure.

FIG. 9B illustrates a surgical loupes head strap 102 including sleeves 106 configured to couple a first monofilament 104a and a second monofilament 104b, in accordance with an example embodiment of the present disclosure. As noted previously herein, surgical loupes head strap 102 may be configured to be adjusted in order to fit heads of various shapes and sizes. For example, in order to contract the size of the surgical loupes head strap 102 and optimize a fit for a wearer with a smaller head, the wearer may grasp the first stopper 108a and the second stopper 108b and pull the ends of the first monofilament 104a and the second monofilament "outwards," away from the sleeve 106, thereby translating the first monofilament 104a and the second monofilament 104b within the sleeve 106 and contracting the size of the surgical loupes head strap 102.

Figure 10A:
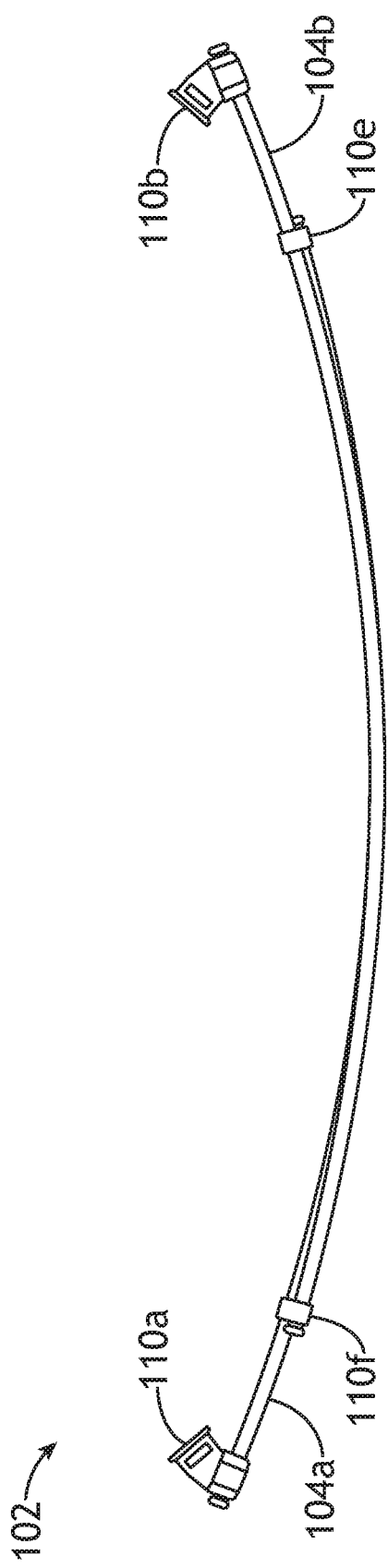
FIG. 10A illustrates a surgical loupes head strap including couplers to couple a first monofilament and a second monofilament, in accordance with an example embodiment of the present disclosure.
Figure 10B:
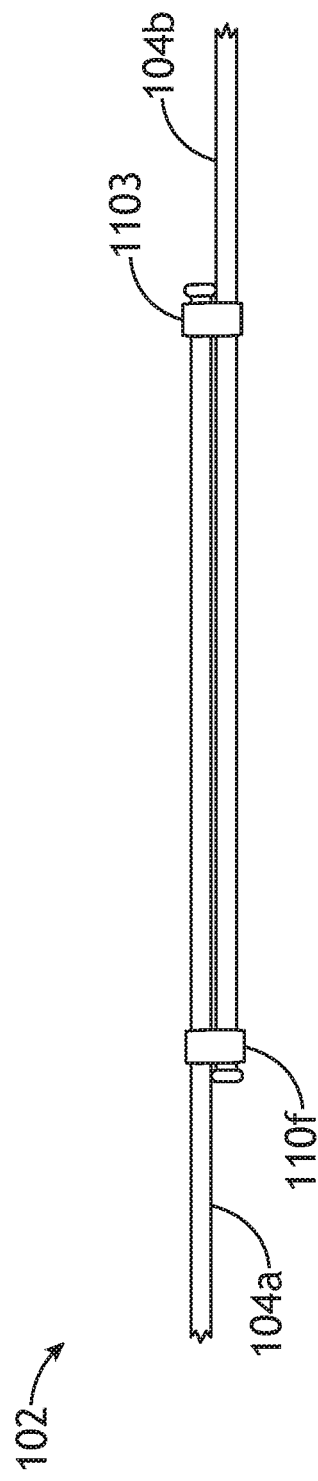
FIG. 10B illustrates a surgical loupes head strap including couplers to couple a first monofilament and a second monofilament, in accordance with an example embodiment of the present disclosure.

FIG. 10A illustrates a surgical loupes head strap 102 including couplers 110e, 110f to couple a first monofilament 104a and a second monofilament 104b, in accordance with an example embodiment of the present disclosure. FIG. 10B illustrates a surgical loupes head strap 102 including couplers to couple a first monofilament and a second monofilament, in accordance with an example embodiment of the present disclosure. As noted previously herein, one or more sleeves 106 may be used to couple the first monofilament 104a and the second monofilament 104b. In additional and/or alternative embodiments, one or more couplers 110 may be configured to couple the first monofilament 104a and the second monofilament 104b. For example, as shown in FIG. 10A, a coupler 110e may be disposed at an end of the first monofilament 104a. For instance, a first hole 122a of coupler 110e may be configured to surround and couple to the end of the first monofilament 104a. A second hole 122b of the coupler 110e may be configured to surround at least a portion of the second monofilament 104b, thereby coupling the first monofilament 104a and the second monofilament. Similarly, a coupler 110f may be disposed at an end of the second monofilament 104b, and configured to couple the second monofilament 104b to the first monofilament 104a.

Figure 11:
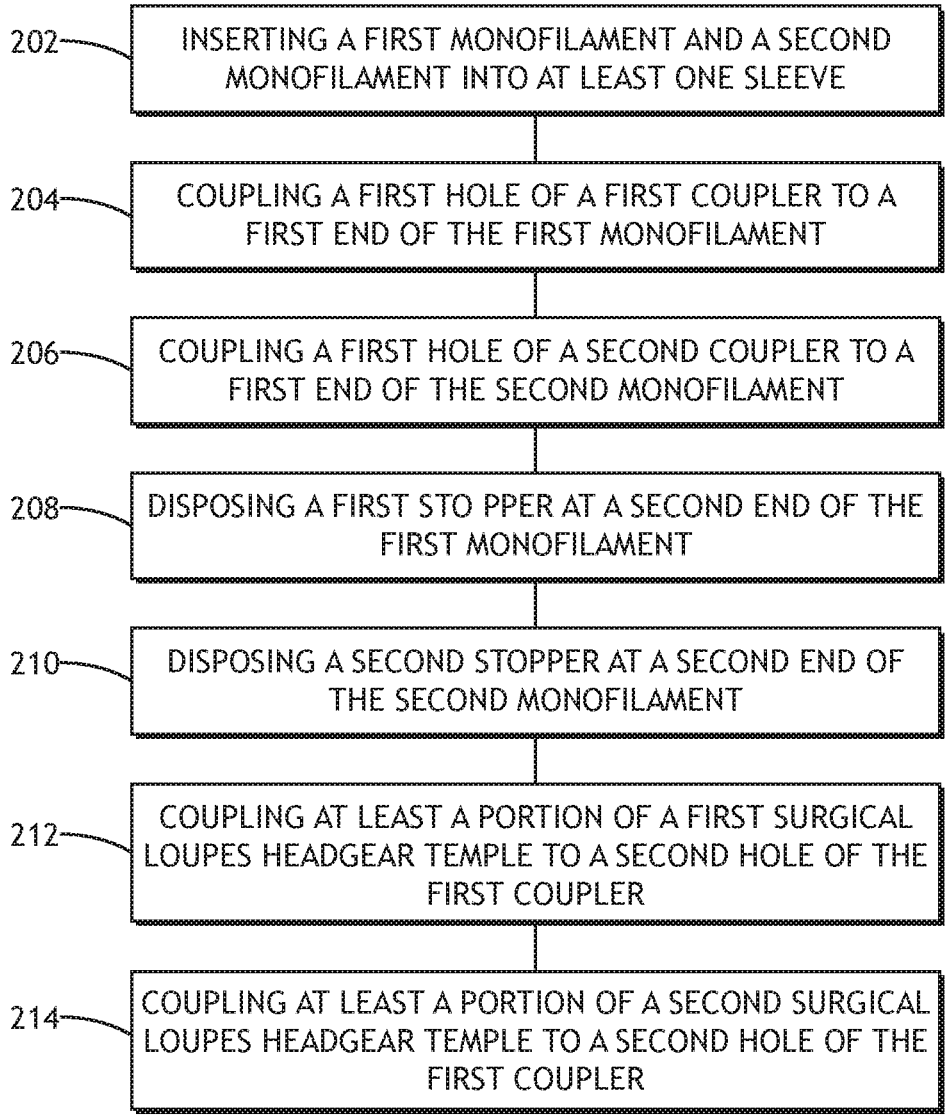
FIG. 11 is a flow diagram illustrating an example implementation of a method for forming a surgical loupes headgear.

FIG. 11 is a flow diagram illustrating an example implementation of a method 200 for forming a surgical loupes headgear 100, in accordance with an example embodiment of the present disclosure. In general, operations of disclosed processes (e.g., method 200) may be performed in an arbitrary order, unless otherwise provided herein.

The method 200 includes inserting a first monofilament and a second monofilament into at least one sleeve (block 202). For example, as shown in FIGS. 9A-9B, a first monofilament 104a and a second monofilament 104b may be inserted into a first sleeve 106a and a second sleeve 106b. In additional and/or alternative embodiment, one or more couplers 110 (e.g., couplers 110e, 110f) may be used to couple the first monofilament 104a and the second monofilament 104b. In embodiments, the first monofilament 104a and the second monofilament 104b are adjustably actuatable within the one or more sleeves 106 (or couplers 110e, 110f).

The method 200 further includes coupling a first hole of a first coupler to a first end of the first monofilament (block 204) and coupling a first hole of a second coupler to a first end of the second monofilament (block 206). For example, as shown in FIGS. 9A-9B, a first hole 122a of a first coupler 110a may be coupled to a first end of the first monofilament 104a, and a first hole 122a of a second coupler 110b may be coupled to a first end of the second monofilament 104b.

The method 200 further includes disposing a first stopper at a second end of the first monofilament (block 208), and disposing a second stopper at a second end of the second monofilament (block 210). The stoppers 108 may include any stopper known in the art configured to prevent the ends of the monofilaments 104 from sliding through the sleeve 106. Stoppers 108 may be formed of metal, plastic, rubber, and the like. Additionally, stoppers 108 may be formed by expanding the ends of the monofilaments 104. In this regard, the first stopper 108a and the second stopper 108b may include expanded portions of the monofilaments 104 and/or physical devices disposed at the ends of the monofilaments 104. For example, disposing a first stopper 108a at a second end of the first monofilament 104a may include heating or burning the second end of the first monofilament 104a.

The method 200 further includes coupling at least a portion of a first surgical loupes headgear temple to a second hole of the first coupler (block 212), and coupling at least a portion of a second surgical loupes headgear temple to a second hole of the second coupler (block 214). For example, as shown in FIG. 1, a second hole 122b of the first coupler 110a may surround and couple to at least a portion of the first temple 107a, and a second hole 122b of the second coupler 110b may surround and couple to at least a portion of the second temple 107b.

The method 200 may further include any step or operation implied or required by the embodiments of surgical loupes headgear 100 described herein. Similarly, the surgical loupes headgear 100 may also include any additional component or functionality expressed or implied by the method 200.

Although the technology has been described with reference to the embodiments illustrated in the attached drawing figures, equivalents may be employed and substitutions made herein without departing from the scope of the technology as recited in the claims. Components illustrated and described herein are merely examples of a device and components that may be used to implement the embodiments of the present invention and may be replaced with other devices and components without departing from the scope of the invention. Furthermore, any dimensions, degrees, and/or numerical ranges provided herein are to be understood as non-limiting examples unless otherwise specified in the claims.

What is claimed is:

1. A surgical loupes head strap, comprising:
  a first monofilament with a first end and a second end;
  a second monofilament with a first end and a second end;
  at least one sleeve configured to couple the first monofilament and the second monofilament;
  a first coupler with a first hole and a second hole, the first hole of the first coupler extending all the way through the first coupler and configured to surround and couple to the first end of the first monofilament which extends all the way through the first hole of the first coupler, wherein the first end of the first monofilament is thermally expanded to retain the first end of the first monofilament within the first hole of the first coupler, the second hole of the first coupler also extending all the way through the first coupler and configured to surround and couple to at least a portion of a first surgical loupes headgear temple which extends all the way through the second hole of the first coupler, wherein the second hole of the first coupler comprises an adjustable coupler including a zip-tie configured to adjustably surround the first temple of the frame; and
  a second coupler with a first hole and a second hole, the first hole of the second coupler extending all the way through the second coupler and configured to surround and couple to the first end of the second monofilament which extends all the way through the first hole of the second coupler, wherein the first end of the second monofilament is thermally expanded to retain the first end of the second monofilament within the first hole of the second coupler, the second hole of the second coupler also extending all the way through the second coupler and configured to surround and couple to at least a portion of a second surgical loupes headgear temple which extends all the way through the second hole of the second coupler, wherein the second hole of the second coupler comprises a second adjustable coupler including a second zip-tie configured to adjustably surround the second temple of the frame,
  wherein a central axis of the first hole of the first coupler and a central axis of the second hole of the first coupler are non-parallel with an offset angle in the range of 10 to 60 degrees between the central axis of the first hole of the first coupler and the central axis of the second hole of the first coupler, and wherein a central axis of the first hole of the second coupler and a central axis of the second hole of the second coupler are also non-parallel with an offset angle in the range of 10 to 60 degrees between the central axis of the first hole of the second coupler and the central axis of the second hole of the second coupler.

2. The surgical loupes head strap of claim 1, further comprising:
  a first stopper disposed at the second end of the first monofilament; and
  a second stopper disposed at the second end of the second monofilament.

3. The surgical loupes head strap of claim 1, wherein the at least one sleeve comprises polyethylene tubing.

4. The surgical loupes head strap of claim 1, wherein the first monofilament and the second monofilament comprise extruded nylon.

5. The surgical loupes head strap of claim 1, wherein the first monofilament and the second monofilament are configured to be adjustably translated within the at least one sleeve in order to adjust the size of the surgical loupes head strap.

6. A surgical loupes headgear, comprising:
  surgical loupes;
  a frame configured to support the surgical loupes, the frame including a first temple and a second temple; and
  a surgical loupes head strap including:
    a first monofilament with a first end and a second end;
    a second monofilament with a first end and a second end;
    at least one sleeve configured to couple the first monofilament and the second monofilament, wherein the first monofilament and the second monofilament are configured to be adjustably translated within the at least one sleeve in order to adjust the size of the surgical loupes head strap;

a first coupler with a first hole and a second hole, the first hole of the first coupler extending all the way through the first coupler and configured to surround and couple to the first end of the first monofilament which extends all the way through the first hole of the first coupler, wherein the first end of the first monofilament is thermally expanded to retain the first end of the first monofilament within the first hole of the first coupler, the second hole of the first coupler also extending all the way through the first coupler and configured to surround and couple to at least a portion of the first temple which extends all the way through the second hole of the first coupler, wherein the second hole of the first coupler comprises an adjustable coupler including a zip-tie configured to adjustably surround the first temple of the frame; and a second coupler with a first hole and a second hole, the first hole of the second coupler extending all the way through the second coupler and configured to surround and couple to the first end of the second monofilament which extends all the way through the first hole of the second coupler, wherein the first end of the second monofilament is thermally expanded to retain the first end of the second monofilament within the first hole of the second coupler, the second hole of the second coupler also extending all the way through the second coupler and configured to surround and couple to at least a portion of the second temple which extends all the way through the second hole of the second coupler, wherein the second hole of the second coupler comprises a second adjustable coupler including a second zip-tie configured to adjustably surround the second temple of the frame, wherein a central axis of the first hole of the first coupler and a central axis of the second hole of the first coupler are non-parallel with an offset angle in the range of 10 to 60 degrees between the central axis of the first hole of the first coupler and the central axis of the second hole of the first coupler, and wherein a central axis of the first hole of the second coupler and a central axis of the second hole of the second coupler are also non-parallel with an offset angle in the range of 10 to 60 degrees between the central axis of the first hole of the second coupler and the central axis of the second hole of the second coupler.

7. The surgical loupes headgear of claim 6, further comprising:
a first stopper disposed at the second end of the first monofilament; and
a second stopper disposed at the second end of the second monofilament.

8. The surgical loupes headgear of claim 6, wherein the at least one sleeve comprises polyethylene tubing.

9. The surgical loupes headgear of claim 6, wherein the first monofilament and the second monofilament comprise extruded nylon.

* * * * *